US010519374B2

(12) United States Patent
Katoh et al.

(10) Patent No.: US 10,519,374 B2
(45) Date of Patent: Dec. 31, 2019

(54) POLYMERIZABLE COMPOSITION CONTAINING POLYMERIZABLE COMPOUND, FILM, HALF MIRROR FOR DISPLAYING PROJECTION IMAGE, AND POLYMERIZABLE COMPOUND

(71) Applicant: FUJIFILM Corporation, Tokyo (JP)

(72) Inventors: Shunya Katoh, Minami-ashigara (JP); Yuki Nakazawa, Minami-ashigara (JP); Masaru Yoshikawa, Minami-ashigara (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/840,655

(22) Filed: Dec. 13, 2017

(65) Prior Publication Data
US 2018/0100103 A1 Apr. 12, 2018

Related U.S. Application Data

(63) Continuation of application No. PCT/JP2016/070209, filed on Jul. 8, 2016.

(30) Foreign Application Priority Data

Jul. 9, 2015 (JP) ................. 2015-137898

(51) Int. Cl.
*C09K 19/30* (2006.01)
*B32B 27/00* (2006.01)
*B32B 27/30* (2006.01)
*B32B 27/38* (2006.01)
*C08F 220/30* (2006.01)
*G02B 1/11* (2015.01)
*G02B 5/30* (2006.01)
*B32B 7/12* (2006.01)
*C08J 5/18* (2006.01)
*C09K 19/38* (2006.01)
(Continued)

(52) U.S. Cl.
CPC ............ *C09K 19/3068* (2013.01); *B32B 7/12* (2013.01); *B32B 27/00* (2013.01); *B32B 27/30* (2013.01); *B32B 27/38* (2013.01); *C07C 69/757* (2013.01); *C07C 69/86* (2013.01); *C08F 220/30* (2013.01); *C08J 5/18* (2013.01); *C08J 7/047* (2013.01); *C09K 19/3809* (2013.01); *C09K 19/56* (2013.01); *G02B 1/11* (2013.01); *G02B 5/30* (2013.01); *B32B 2307/416* (2013.01); *B32B 2307/704* (2013.01); *B32B 2551/08* (2013.01); *C07C 2601/14* (2017.05); *C08J 2333/14* (2013.01); *C08J 2367/02* (2013.01); *C08J 2433/14* (2013.01); *C09K 2019/0448* (2013.01); *C09K 2019/3075* (2013.01); *C09K 2211/1007* (2013.01); *C09K 2211/1425* (2013.01); *G02B 1/111* (2013.01); *Y10T 428/10* (2015.01); *Y10T 428/1036* (2015.01)

(58) Field of Classification Search
CPC ............ C09K 19/3068; C09K 19/3809; C09K 2019/3075; C09K 2019/0448; C09K 2211/1007; B32B 27/00; B32B 27/30; B32B 27/38; C08F 220/30; G02B 1/111; C08J 5/18; C08J 2333/14; C08J 2367/02
USPC .......... 428/1.1, 1.3, 1.33, 1.6; 349/117, 118; 252/299.01, 299.63; 560/84
See application file for complete search history.

(56) References Cited

U.S. PATENT DOCUMENTS

2007/0102669 A1* 5/2007 Kaida ................... C08F 220/30
252/299.01
2008/0081133 A1 4/2008 Kato
(Continued)

FOREIGN PATENT DOCUMENTS

JP 2004-262884 A 9/2004
JP 2005-179557 A 7/2005
(Continued)

OTHER PUBLICATIONS

Office Action dated Nov. 6, 2018 issued by the Japanese Patent Office in counterpart Japanese application No. 2017-527504.
(Continued)

*Primary Examiner* — Ruiyun Zhang
(74) *Attorney, Agent, or Firm* — Sughrue Mion, PLLC

(57) ABSTRACT

The present invention provides a polymerizable composition containing at least two types of polymerizable compounds represented by Formula (I),

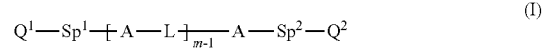

in the formula, A represents a phenylene group or a trans-1,4-cyclohexylene group, L represents —OC(=O)—, —OC(=O)O—, and the like, m represents 3 to 12, $Sp^1$ and $Sp^2$ represent a linking group, and $Q^1$ and $Q^2$ represent a polymerizable group, and the like, in which in a case where a number obtained by dividing the number of trans-1,4-cyclohexylene groups by m is set to mc, mc's for the two types of polymerizable compounds are different from each other, at least one of the two types of the polymerizable compounds satisfies 0.5<mc<0.7, and at least the other of the two types of the polymerizable compounds satisfies 0.5<mc; and a polymerizable compound in which m in Formula (I) is 6 to 12. It is possible to provide a film such as a low birefringence phase difference film or a reflection film having high selectivity in a reflection wavelength range by using the polymerizable composition.

20 Claims, No Drawings

(51) Int. Cl.
*C09K 19/56* (2006.01)
*C08J 7/04* (2006.01)
*C07C 69/757* (2006.01)
*C07C 69/86* (2006.01)
*G02B 1/111* (2015.01)
*C09K 19/04* (2006.01)

(56) References Cited

U.S. PATENT DOCUMENTS

2016/0115338 A1 4/2016 Kuwana et al.
2016/0318845 A1 11/2016 Katoh et al.
2017/0009138 A1* 1/2017 Nakazawa ......... C09K 19/3068
2017/0190821 A1 7/2017 Shunya et al.

FOREIGN PATENT DOCUMENTS

| JP | 2008-100982 A | 5/2008 |
| JP | 2010-270108 A | 12/2010 |
| JP | 2013-112631 A | 6/2013 |
| JP | 2015-163596 A | 9/2015 |
| WO | 2006/001097 A1 | 1/2006 |
| WO | 2014/192655 A1 | 12/2014 |
| WO | 2016/047648 A1 | 3/2016 |

OTHER PUBLICATIONS

International Preliminary Report on Patentability dated Jan. 16, 2017, from the International Bureau in counterpart International Application No. PCT/JP2016/070209.
Written Opinion dated Aug. 9, 2016, from the International Bureau in counterpart International Application No. PCT/JP2016/070209.
International Search Report dated Aug. 9, 2016, from the International Bureau in counterpart International Application No. PCT/JP2016/070209.

* cited by examiner

POLYMERIZABLE COMPOSITION CONTAINING POLYMERIZABLE COMPOUND, FILM, HALF MIRROR FOR DISPLAYING PROJECTION IMAGE, AND POLYMERIZABLE COMPOUND

CROSS-REFERENCE TO RELATED APPLICATIONS

This application is a continuation of PCT International Application No. PCT/JP2016/070209 filed on Jul. 8, 2016, which claims priority under 35 U.S.C § 119 (a) to Japanese Patent Application No. 2015-137898 filed on Jul. 9, 2015, the entire content of which is incorporated herein by reference.

BACKGROUND OF THE INVENTION

1. Field of the Invention

The present invention relates to a polymerizable composition containing a polymerizable compound. In addition, the present invention relates to a film which is prepared by using the polymerizable composition, and a half mirror for displaying a projection image which is prepared by using the polymerizable composition. The present invention further relates to a new polymerizable compound.

2. Description of the Related Art

It is possible to prepare various optical films such as a phase difference film or a reflection film by using a polymerizable compound having liquid crystallinity. The birefringence of the polymerizable compound is one of properties closely associated with the optical properties of an optical film to be obtained. For example, it is possible to obtain a reflection film having high selectivity in a reflection wavelength range with a film which is formed by using a polymerizable compound having low birefringence and by immobilizing a cholesteric liquid crystalline phase. In JP2004-262884A, it is disclosed that a low birefringence phase difference film, or a reflection film having high selectivity in a reflection wavelength range is obtained by using a non-liquid crystalline (meth)acrylate compound having a specific structure along with a polymerizable liquid crystal compound.

SUMMARY OF THE INVENTION

In a case where an optical film using a polymerizable compound having liquid crystallinity is prepared, there is a case where two or more types of polymerizable compounds are used by being combined in order to obtain necessary birefringence or reflection properties at a constant film thickness. However, in the related art, a preferred range of the combination was not considered. The present inventors have found that a polymerizable compound which contains a plurality of cyclic groups having a trans-1,4-cyclohexylene group exhibits low birefringence, but in the related art, it was not considered that liquid crystallinity is controlled according to how a plurality of polymerizable compounds including the compound found by the present inventors are combined, and thus, a film having necessary birefringence or wavelength selectivity is obtained.

An object of the present invention, in particular, is to provide a polymerizable composition which contains two or more types of polymerizable compounds having a trans-1,4-cyclohexylene group and a phenylene group, and has low birefringence. In addition, another object of the present invention is to provide a film such as a low birefringence phase difference film or a reflection film having high selectivity in a reflection wavelength range by using the polymerizable composition described above. A still another object of the present invention is to provide a new polymerizable compound which is used for the polymerizable composition.

The present inventors have conducted various studies in order to attain the objects described above, have found that a ratio of a trans-1,4-cyclohexylene group to a phenylene group of each compound to be combined is controlled, and thus, liquid crystallinity or birefringence of a polymerizable composition containing the compound can be controlled, have further conducted studies on the basis of the findings, and thus, have completed the present invention.

That is, the present invention provides <1> to <22> described below.

<1> A polymerizable composition, comprising:
at least two types of polymerizable compounds represented by Formula (I);

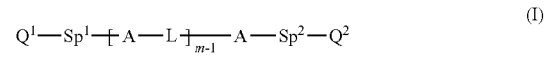

in the formula, A represents a phenylene group which may have a substituent or a trans-1,4-cyclohexylene group which may have a substituent, L represents a single bond or a linking group selected from the group consisting of $-CH_2O-$, $-OCH_2-$, $-(CH_2)_2OC(=O)-$, $-C(=O)O(CH_2)_2-$, $-C(=O)O-$, $-OC(=O)-$, $-OC(=O)O-$, $-CH=CH-C(=O)O-$, and $-OC(=O)-CH=CH-$, m represents an integer of 3 to 12, $Sp^1$ and $Sp^2$ each independently represent a single bond or a linking group selected from the group consisting of a linear alkylene group or a branched alkylene group having 1 to 20 carbon atoms, and a group in which one or two or more $-CH_2-$'s in the linear alkylene group or the branched alkylene group having 1 to 20 carbon atoms are substituted with $-O-$, $-S-$, $-NH-$, $-N(CH_3)-$, $-C(=O)-$, $-OC(=O)-$, or $-C(=O)O-$, and $Q^1$ and $Q^2$ each independently represent a hydrogen atom or a polymerizable group selected from the group consisting of groups represented by Formula Q-1 to Formula Q-5, and any one of $Q^1$ and $Q^2$ represents a polymerizable group,

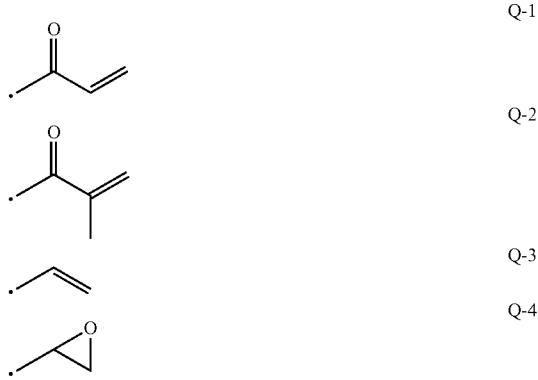

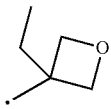

in which in a case where a number obtained by dividing the number of trans-1,4-cyclohexylene groups which may have a substituent and are represented by A by m is set to mc, mc's for the two types of polymerizable compounds are different from each other, at least one of the two types of the polymerizable compounds satisfies 0.5<mc<0.7, and at least the other of the two types of the polymerizable compounds satisfies 0.5<mc.

<2> The polymerizable composition according to <1>, in which at least one of the two types of the polymerizable compounds satisfies 0.5<mc<0.65.

<3> The polymerizable composition according to <1> or <2>, in which in Formula (I), the substituent that the phenylene group and the trans-1,4-cyclohexylene group may have is selected from the group consisting of an alkyl group, an alkoxy group, and a group represented by —C(=O)—$X^3$-$Sp^3$-$Q^3$, and here, $X^3$ represents a single bond, —O—, —S—, or —N($Sp^4$-$Q^4$)—, or represents a nitrogen atom which forms a ring structure along with $Q^3$ and $Sp^3$, $Sp^3$ and $Sp^4$ each independently represent a single bond or a linking group selected from the group consisting of a linear alkylene group or a branched alkylene group having 1 to 20 carbon atoms, and a group in which one or two or more —CH$_2$—'s in the linear alkylene group or the branched alkylene group having 1 to 20 carbon atoms are substituted with —O—, —S—, —NH—, —N(CH$_3$)—, —C(=O)—, —OC(=O)—, or —C(=O)O—, and $Q^3$ and $Q^4$ each independently represent a hydrogen atom, a cycloalkyl group, a group in which one or two or more —CH$_2$—'s in the cycloalkyl group are substituted with —O—, —S—, —NH—, —N(CH$_3$)—, —C(=O)—, —OC(=O)—, or —C(=O)O—, or any one polymerizable group selected from the group consisting of groups represented by Formula Q-1 to Formula Q-5.

in the formula, $R^1$ and $R^2$ are each independently selected from the group consisting of a hydrogen atom, an alkyl group, an alkoxy group, and a group represented by —C(=O)—$X^3$-$Sp^3$-$Q^3$, and here, $X^3$ represents a single bond, —O—, —S—, or —N($Sp^4$-$Q^4$)—, or represents a nitrogen atom which forms a ring structure along with $Q^3$ and $Sp^3$, $Sp^3$ and $Sp^4$ each independently represent a single bond or a linking group selected from the group consisting of a linear alkylene group or a branched alkylene group having 1 to 20 carbon atoms, and a group in which one or two or more —CH$_2$—'s in the linear alkylene group or the branched alkylene group having 1 to 20 carbon atoms are substituted with —O—, —S—, —NH—, —N(CH$_3$)—, —C(=O)—, —OC(=O)—, or —C(=O)O—, and $Q^3$ and $Q^4$ each independently represent a hydrogen atom, a cycloalkyl group, a group in which one or two or more —CH$_2$—'s in the cycloalkyl group are substituted with —O—, —S—, —NH—, —N(CH$_3$)—, —C(=O)—, —OC(=O)—, or —C(=O)O—, or any one polymerizable group selected from the group consisting of groups represented by Formula Q-1 to Formula Q-5.

<5> The polymerizable composition according to <4>, in which $R^1$ and $R^2$ are each independently —C(=O)—$X^3$-$Sp^3$-$Q^3$, and $X^3$ is —O—.

<6> The polymerizable composition according to <4> or <5>, in which $R^1$ and $R^2$ are identical to each other.

<7> The polymerizable composition according to any one of <1> to <6>, in which all of the polymerizable compounds satisfy 0.5<mc<0.7.

<8> The polymerizable composition according to any one of <1> to <7>, in which the compound represented by Formula (I) is a compound represented by Formula (V);

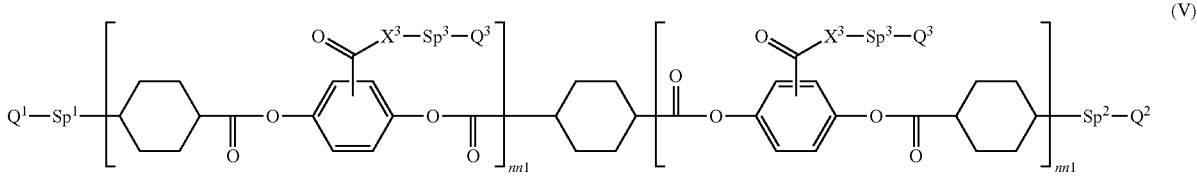

<4> The polymerizable composition according to any one of <1> to <3>, in which the polymerizable composition includes at least one type of the compound which is represented by Formula (I) and has a partial structure represented by Formula (II);

in the formula, nn1 and nn2 each independently represent an integer of 1 or 2 and values represented by nn1+nn2 in the two types of the polymerizable compounds are different from each other.

<9> The polymerizable composition according to any one of <1> to <8>, further comprising: a cross-linking agent.

<10> The polymerizable composition according to any one of <1> to <9>, further comprising: a polymerization initiator.

<11> The polymerizable composition according to any one of <1> to <10>, further comprising: a chiral compound.

<12> A film, comprising: a layer obtained by curing the polymerizable composition according to any one of <1> to <11>.

<13> A film, comprising: two or more layers obtained by curing the polymerizable composition according to any one of <1> to <11>.

<14> The film according to <12> or <13>, in which the film exhibits selective reflection, and Δλ/λ which is a ratio of a half-width Δλ of a wavelength range of the selective reflection to a center wavelength λ of the selective reflection is less than or equal to 0.09.

<15> The film according to any one of <12> to <14>, in which the film reflects visible light.

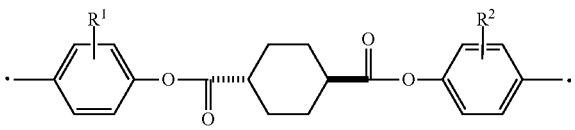

<16> A film, comprising: at least three layers obtained by curing the polymerizable composition according to any one of <1> to <11>, in which the three layers are a layer formed by immobilizing a cholesteric liquid crystalline phase having a center wavelength of selective reflection in a red light wavelength range, a layer formed by immobilizing a cholesteric liquid crystalline phase having a center wavelength of selective reflection in a green light wavelength range, and a layer formed by immobilizing a cholesteric liquid crystalline phase having a center wavelength of selective reflection in a blue light wavelength range.

<17> A half mirror for displaying a projection image, comprising: the film according to <16>.

<18> The half mirror for displaying a projection image according to <17>, further comprising: a base material which is inorganic glass or an acrylic resin.

<19> The half mirror for displaying a projection image according to <17> or <18>, further comprising: an antireflection layer on an outermost surface.

<20> A polymerizable compound which is represented by Formula (I);

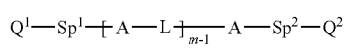  (I)

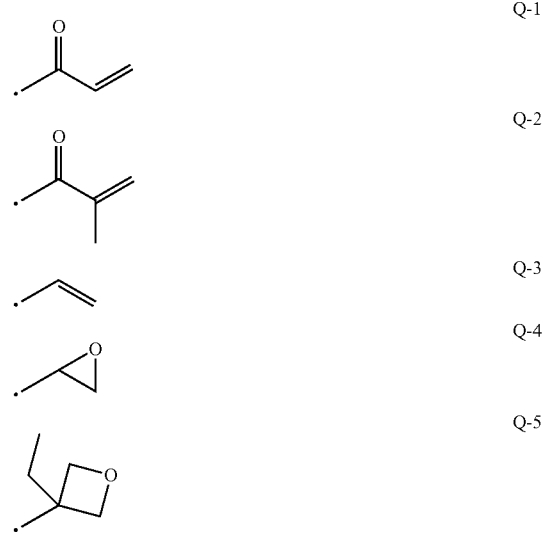

<21> The polymerizable compound according to <20>, in which m is 7 or 9.

<22> The polymerizable compound according to <21>, which is represented by Formula (V);

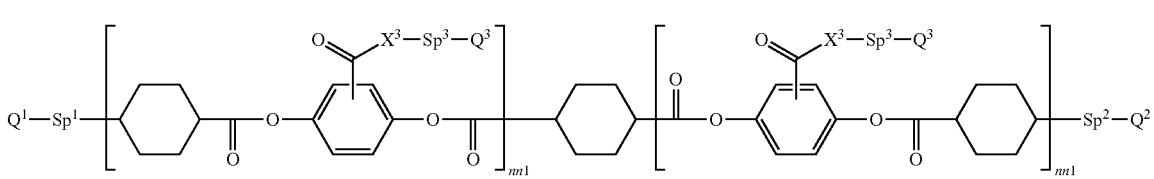 (V)

in the formula, A represents a phenylene group which may have a substituent or a trans-1,4-cyclohexylene group which may have a substituent, L represents a single bond or a linking group selected from the group consisting of —CH$_2$O—, —OCH$_2$—, —(CH$_2$)$_2$OC(=O)—, —C(=O)O(CH$_2$)$_2$—, —C(=O)O—, —OC(=O)—, —OC(=O)O—, —CH=CH—C(=O)O—, and —OC(=O)—CH=CH—, m represents an integer of 6 to 12, in a case where a number obtained by dividing the number of trans-1,4-cyclohexylene groups which may have a substituent and are represented by A by m is set to mc, 0.5<mc<0.7 is satisfied, Sp$^1$ and Sp$^2$ each independently represent a single bond or a linking group selected from the group consisting of a linear alkylene group or a branched alkylene group having 1 to 20 carbon atoms, and a group in which one or two or more —CH$_2$—'s in the linear alkylene group or the branched alkylene group having 1 to 20 carbon atoms are substituted with —O—, —S—, —NH—, —N(CH$_3$)—, —C(=O)—, —OC(=O)—, or —C(=O)O—, and Q$^1$ and Q$^2$ each independently represent a hydrogen atom or a polymerizable group selected from the group consisting of groups represented by Formula Q-1 to Formula Q-5, and any one of Q$^1$ and Q$^2$ represents a polymerizable group.

in the formula, Sp$^1$ and Sp$^2$ each independently represent a single bond or a linking group selected from the group consisting of a linear alkylene group or a branched alkylene group having 1 to 20 carbon atoms, and a group in which one or two or more —CH$_2$—'s in the linear alkylene group or the branched alkylene group having 1 to 20 carbon atoms are substituted with —O—, —S—, —NH—, —N(CH$_3$)—, —C(=O)—, —OC(=O)—, or —C(=O)O—, Q$^1$ and Q$^2$ each independently represent a hydrogen atom or a polymerizable group selected from the group consisting of groups represented by Formula Q-1 to Formula Q-5, and any one of Q$^1$ and Q$^2$ represents a polymerizable group,

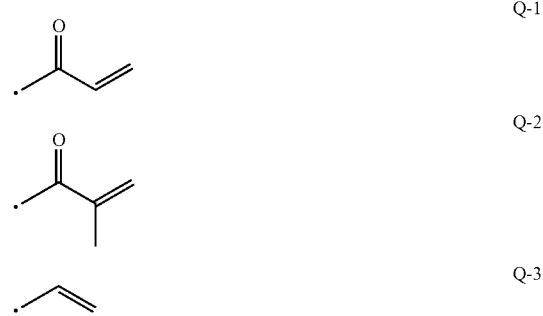

-continued

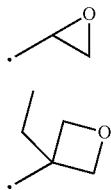

X³ represents a single bond, —O—, —S—, or —N(Sp⁴-Q⁴)—, or represents a nitrogen atom which forms a ring structure along with Q³ and Sp³, Sp³ and Sp⁴ each independently represent a single bond or a linking group selected from the group consisting of a linear alkylene group or a branched alkylene group having 1 to 20 carbon atoms, and a group in which one or two or more —CH₂—'s in the linear alkylene group or the branched alkylene group having 1 to 20 carbon atoms are substituted with —O—, —S—, —NH—, —N(CH₃)—, —C(=O)—, —OC(=O)—, or —C(=O)O—, and Q³ and Q⁴ each independently represent a hydrogen atom, a cycloalkyl group, a group in which one or two or more —CH₂—'s in the cycloalkyl group are substituted with —O—, —S—, —NH—, —N(CH₃)—, —C(=O)—, —OC(=O)—, or —C(=O)O—, or any one polymerizable group selected from the group consisting of groups represented by Formula Q-1 to Formula Q-5, and nn1 and nn2 each independently represent an integer of 1 or 2, and nn1+nn2 is 3 or 4.

According to the present invention, a polymerizable composition having low birefringence is provided as a polymerizable composition which contains two or more types of polymerizable compounds having a trans-1,4-cyclohexylene group and a phenylene group. It is possible to provide a film such as a low birefringence phase difference film or a reflection film having high selectivity in a reflection wavelength range by using the polymerizable composition of the present invention. In addition, according to the present invention, a new polymerizable compound is provided.

DESCRIPTION OF THE PREFERRED EMBODIMENTS

Hereinafter, the present invention will be described in detail. Furthermore, herein, a numerical range represented by using "to" indicates a range including the numerical values before and after "to" as the lower limit value and the upper limit value.

Herein, "(meth)acrylate" indicates "any one or both of acrylate and methacrylate". The same applies to "(meth)acryl group" or the like, and "(meth)acryloyl group" indicates "any one or both of an acryloyl group and a methacryloyl group".

Herein, a "liquid crystal layer" indicates a layer formed by using a liquid crystal composition containing a polymerizable liquid crystal compound, and, in particular, a layer obtained by curing a liquid crystal composition containing a polymerizable liquid crystal compound. In the liquid crystal layer, it is sufficient that the optical properties of the liquid crystalline phase are retained in the layer, and finally, it is not necessary that the composition in the cured film has liquid crystallinity. For example, the composition may have a high molecular weight by the curing reaction, and may lose the liquid crystallinity.

Herein, a phase difference indicates in-plane retardation, and indicates in-plane retardation at a wavelength of 550 nm, unless otherwise a wavelength is stated. Herein, the in-plane retardation is measured by using a polarization phase difference analysis device AxoScan manufactured by Axometrics, Inc. The in-plane retardation at a wavelength of λ nm can be measured by allowing light at a wavelength of λ nm to be incident in a film normal direction using KOBRA 21ADH or WR (manufactured by Oji Scientific Instruments).

<Polymerizable Composition>

A polymerizable composition of the present invention contains a polymerizable compound represented by Formula (I).

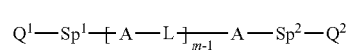

The polymerizable composition of the present invention may contain other components such as other liquid crystal compounds, a chiral compound, a polymerization initiator, and an alignment control agent, in addition to the polymerizable compound represented by Formula (I). Hereinafter, each component will be described.

[Polymerizable Compound Represented by Formula (I)]

The polymerizable compound represented by Formula (I) has m cyclic divalent groups represented by A.

m represents an integer of 3 to 12, is preferably an integer of 3 to 9, and is more preferably an integer of 3, 5, 7, or 9.

m A's may be identical to each other or different from each other. The cyclic divalent group represented by A is a phenylene group which may have a substituent or a trans-1,4-cyclohexylene group which may have a substituent. That is, A represents a phenylene group which may have a substituent or a trans-1,4-cyclohexylene group which may have a substituent. Herein, when A is a phenylene group, a 1,4-phenylene group is preferable.

The polymerizable composition of the present invention may contain at least one type of the polymerizable compound represented by Formula (I) having a phenylene group which may have at least one substituent and a trans-1,4-cyclohexylene group which may have at least one substituent.

In Formula (I), the substituent of the phenylene group and the trans-1,4-cyclohexylene group "which may have a substituent" is not particularly limited, and examples of the substituent include a substituent selected from the group consisting of an alkyl group, a cycloalkyl group, an alkoxy group, an alkyl ether group, an amido group, an amino group, a halogen atom, and a group configured by combining two or more substituents described above. In addition, examples of the substituent include a substituent represented by —C(=O)—X³-Sp³-Q³ described below. The phenylene group and the trans-1,4-cyclohexylene group may have 1 to 4 substituents. When the phenylene group and the trans-1,4-cyclohexylene group have two or more substituents, the two or more substituents may be identical to each other or different from each other. The phenylene group preferably has one or two substituents and more preferably has only one substituent. The trans-1,4-cyclohexylene group preferably does not have a substituent.

Herein, the alkyl group may be any one of a linear alkyl group and a branched alkyl group. The number of carbon atoms of the alkyl group is preferably 1 to 30, is more preferably 1 to 10, and is particularly preferably 1 to 6. Examples of the alkyl group can include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a 1,1-dimethyl propyl group, an n-hexyl group, an isohexyl group, a linear heptyl group or a branched heptyl group, an octyl group, a nonyl group, a decyl group, a undecyl group, or a dodecyl group. The same description with respect to the alkyl group described above applies to an alkoxy group including the alkyl group. In addition, herein, in the alkylene group, specific examples of the alkylene group include a divalent group or the like obtained by removing one arbitrary hydrogen atom from each of the examples of the alkyl group described above. Examples of the halogen atom include a fluorine atom, a chlorine atom, a bromine atom, and an iodine atom.

Herein, the number of carbon atoms of the cycloalkyl group is preferably 3 to 20, is more preferably greater than or equal to 5, and is preferably less than or equal to 10, is more preferably less than or equal to 8, and is even more preferably less than or equal to 6. Examples of the cycloalkyl group can include a cyclopropyl group, a cyclobutyl group, a cyclopentyl group, a cyclohexyl group, a cycloheptyl group, and a cyclooctyl group.

In particular, a substituent selected from the group consisting of an alkyl group, an alkoxy group, and —C(═O)—X$^3$-Sp$^3$-Q$^3$ is preferable as the substituent that the phenylene group and the trans-1,4-cyclohexylene group may have. Here, X$^3$ represents a single bond, —O—, —S—, or —N(Sp$^4$-Q$^4$)—, or represents a nitrogen atom which forms a ring structure along with Q$^3$ and Sp$^3$. Sp$^3$ and Sp$^4$ each independently represent a single bond or a linking group selected from the group consisting of a linear alkylene group or a branched alkylene group having 1 to 20 carbon atoms, and a group in which one or two or more —CH$_2$—'s in the linear alkylene group or the branched alkylene group having 1 to 20 carbon atoms are substituted with —O—, —S—, —NH—, —N(CH$_3$)—, —C(═O)—, —OC(═O)—, or —C(═O)O—.

Q$^3$ and Q$^4$ each independently represent a hydrogen atom, a cycloalkyl group, a group in which one or two or more —CH$_2$—'s in the cycloalkyl group are substituted with —O—, —S—, —NH—, —N(CH$_3$)—, —C(═O)—, —OC(═O)—, or —C(═O)O—, or any one polymerizable group selected from the group consisting of groups represented by Formula Q-1 to Formula Q-5.

Specifically, examples of the group in which one or two or more —CH$_2$—'s in the cycloalkyl group are substituted with —O—, —S—, —NH—, —N(CH$_3$)—, —C(═O)—, —OC(═O)—, or —C(═O)O— include a tetrahydrofuranyl group, a pyrrolidinyl group, an imidazolidinyl group, a pyrazolidinyl group, a piperidyl group, a piperazinyl group, a morpholinyl group, and the like. A substitution position is not particularly limited. Among them, the tetrahydrofuranyl group is preferable, and a 2-tetrahydrofuranyl group is particularly preferable.

In Formula (I), L represents a single bond or a linking group selected from the group consisting of —CH$_2$O—, —OCH$_2$—, —(CH$_2$)$_2$OC(═O)—, —C(═O)O(CH$_2$)$_2$—, —C(═O)O—, —OC(═O)—, —OC(═O)O—, —CH═CH—C(═O)O—, and —OC(═O)—CH═CH—.

It is preferable that L is —C(═O)O— or —OC(═O)—. m L's may be identical to each other or different from each other.

Sp$^1$ and Sp$^2$ each independently represent a single bond or a linking group selected from the group consisting of a linear alkylene group or a branched alkylene group having 1 to 20 carbon atoms, and a group in which one or two or more —CH$_2$—'s in the linear alkylene group or the branched alkylene group having 1 to 20 carbon atoms are substituted with —O—, —S—, —NH—, —N(CH$_3$)—, —C(═O)—, —OC(═O)—, or —C(═O)O—. It is preferable that Sp$^1$ and Sp$^2$ are each independently a linking group configured by combining one or two or more groups selected from the group consisting of a linear alkylene group having 1 to 10 carbon atoms in which a linking group selected from the group consisting of —O—, —OC(═O)—, and —C(═O)O— is bonded to both terminals, —OC(═O)—, —C(═O)O—, —O—, and a linear alkylene group having 1 to 10 carbon atoms, and it is more preferable that Sp$^1$ and Sp$^2$ are each independently a linear alkylene group having 1 to 10 carbon atoms in which a linking group selected from the group consisting of —O—, —OC(═O)—, and —C(═O)O— is bonded to each of both terminals.

Q$^1$ and Q$^2$ each independently represent a hydrogen atom or a polymerizable group selected from the group consisting of groups represented by Formula Q-1 to Formula Q-5 below, and any one of Q$^1$ and Q$^2$ represents a polymerizable group.

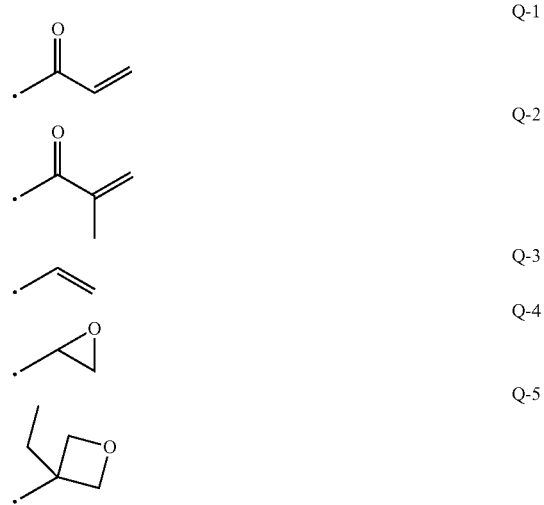

An acryloyl group (Formula Q-1) or a methacryloyl group (Formula Q-2) is preferable as the polymerizable group.

Specifically, examples of the polymerizable compound represented by Formula (I) can include a polymerizable compound represented by Formula (I-11), a polymerizable compound represented by Formula (I-21), and the like, in addition to known compounds described in JP2013-112631A, JP2010-70543A, JP4725516B, and the like.

Polymerizable Compound Represented by Formula (I-11)

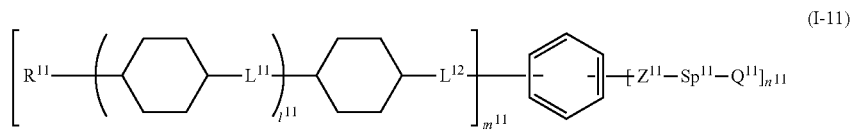

In the formula, $R^{11}$ represents a hydrogen atom, a linear alkyl group or a branched alkyl group having 1 to 12 carbon atoms, or —$Z^{12}$-$Sp^{12}$-$Q^{12}$, $L^{11}$ represents a single bond, —C(=O)O—, or —O(C=O)—, $L^{12}$ represents —C(=O)O—, —OC(=O)—, or —$CONR^2$—, $Z^{11}$ and $Z^{12}$ each independently represent a single bond, —O—, —NH—, —N(CH$_3$)—, —S—, —C(=O)O—, —OC(=O)—, —OC(=O)O—, or —C(=O)NR$^{12}$—, $R^{12}$ represents a hydrogen atom or -$Sp^{12}$-$Q^{12}$, $Sp^{11}$ and $Sp^{12}$ each independently represent a single bond, a linear alkylene group or a branched alkylene group having 1 to 12 carbon atoms which may be substituted with $Q^{11}$, or a linking group obtained by substituting one or more —CH$_2$—'s in the linear alkylene group or the branched alkylene group having 1 to 12 carbon atoms which may be substituted with $Q^{11}$ with —O—, —S—, —NH—, —N($Q^{11}$)—, or —C(=O)—, $Q^{11}$ represents a hydrogen atom, a cycloalkyl group, a group in which one or two or more —CH$_2$—'s in the cycloalkyl group are substituted with —O—, —S—, —NH—, —N(CH$_3$)—, —C(=O)—, —OC(=O)—, or —C(=O)O—, or a polymerizable group selected from the group consisting of groups represented by Formula Q-1 to Formula Q-5, $Q^{12}$ represents a hydrogen atom or a polymerizable group selected from the group consisting of groups represented by Formula Q-1 to Formula Q-5, $l^{11}$ represents an integer of 0 to 2, $m^{11}$ represents an integer of 1 or 2, $n^{11}$ represents an integer of 1 to 3, and a plurality of $R^{11}$'s, a plurality of $L^{11}$'s, a plurality of $L^{12}$'s, a plurality of $l^{11}$'s, a plurality of $Z^{11}$'s, a plurality of $Sp^{11}$'s, and a plurality of $Q^{11}$'s may be respectively identical to each other or different from each other. In addition, the polymerizable compound represented by Formula (I-11) has at least one —$Z^{12}$-$Sp^{12}$-$Q^{12}$, in which $Q^{12}$ is a polymerizable group selected from the group consisting of groups represented by Formula Q-1 to Formula Q-5, as $R^{11}$. It is preferable that the polymerizable compound represented by Formula (I-11) has at least one group selected from the group consisting of —$Z^{11}Sp^{11}$-$Q^{11}$ in which $Z^{11}$ is —C(=O) O— or —C(=O)NR$^{12}$—, and $Q^{11}$ is a polymerizable group selected from the group consisting of groups represented by Formula Q-1 to Formula Q-5, and —$Z^{12}$-$Sp^{12}$-$Q^{12}$ in which $Z^{12}$ is —C(=O)O— or —C(=O)NR$^{12}$—, and $Q^{12}$ is a polymerizable group selected from the group consisting of groups represented by Formula Q-1 to Formula Q-5.

All 1,4-cyclohexylene groups in the polymerizable compound represented by Formula (I-11) are trans-1,4-cyclohexylene groups.

It is also preferable that the polymerizable composition of the present invention contains at least one type of the polymerizable compound represented by Formula (I-11) in which $m^{11}$ is 1, $l^{11}$ is 1 (a dicyclohexyl group), and $Q^{11}$ is a polymerizable group selected from the group consisting of groups represented by Formula Q-1 to Formula Q-5. In this case, it is more preferable that $m^{11}$ is 1.

It is also preferable that the polymerizable composition of the present invention contains at least one type of the polymerizable compound represented by Formula (I-11) in which $m^{11}$ is 2, all of $l^{11}$'s is 0, both of two $R^{11}$'s represent —$Z^{12}$-$Sp^{12}$-$Q^{12}$, and $Q^{12}$ is a polymerizable group selected from the group consisting of groups represented by Formula Q-1 to Formula Q-5.

Moreover, it is also preferable that the polymerizable composition of the present invention contains at least one type of the polymerizable compound represented by Formula (I-11) in which $m^{11}$ is 2, all of $l^{11}$'s is 1, both of two $R^{11}$'s represent —$Z^{12}$-$Sp^{12}$-$Q^{12}$, $Q^{12}$ is a polymerizable group selected from the group consisting of groups represented by Formula Q-1 to Formula Q-5, and both of $L^{11}$ and $L^{12}$ are —C(=O)O— or —O(C=O)—.

Polymerizable Compound Represented by Formula (I-21)

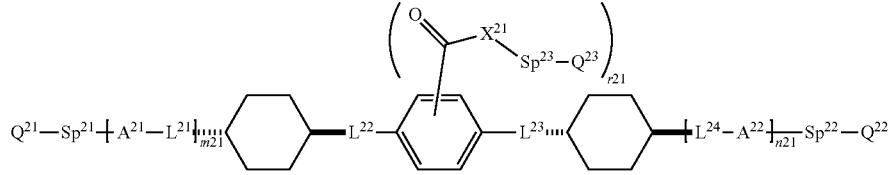

(I-21)

In the formula, $A^{21}$ and $A^{22}$ each independently represent a trans-1,4-cyclohexylene group which may have a substituent and a phenylene group which may have a substituent, all of the substituents described above are each independently 1 to 4 substituents selected from the group consisting of —CO—$X^{21}$-$Sp^{23}$-$Q^{23}$, an alkyl group, and an alkoxy group, m21 represents an integer of 1 or 2, and n21 represents an integer of 0 or 1, when m21 represents 2, n21 represents 0, when m21 represents 2, two $A^{21}$'s may be identical to each other or different from each other, at least one of $A^{21}$ or $A^{22}$ is a phenylene group which may have a substituent, $L^{21}$, $L^{22}$, $L^{23}$, and $L^{24}$ each independently represent a single bond or a linking group selected from the group consisting of —CH$_2$O—, —OCH$_2$—, —(CH$_2$)$_2$OC (=O)—, —C(=O)O(CH$_2$)$_2$—, —C(=O)O—, —OC (=O)—, —OC(=O)O—, —CH=CH—C(=O)O—, and —OC(=O)—CH=CH—, $X^{21}$ represents —O—, —S—, or —N(Sp$^{25}$-Q$^{25}$)—, or represents a nitrogen atom which forms a ring structure along with $Q^{23}$ and $Sp^{23}$, r21 represents an integer of 1 to 4, $Sp^{21}$, $Sp^{22}$, $Sp^{23}$, $Sp^{24}$, and $Sp^{25}$ each independently represent a single bond or a linking group selected from the group consisting of a linear alkylene group or a branched alkylene group having 1 to 20 carbon atoms, and a group in which one or two or more —CH$_2$—'s in the linear alkylene group or the branched alkylene group having 1 to 20 carbon atoms are substituted with —O—, —S—, —NH—, —N(CH$_3$)—, —C(=O)—, —OC(=O)—, or —C(=O) O—, $Q^{21}$ and $Q^{22}$ each independently represent any one polymerizable group selected from the group consisting of groups represented by Formula Q-1 to Formula Q-5, $Q^{23}$ represents a hydrogen atom, a cycloalkyl group, a group in which one or two or more —CH$_2$—'s in the cycloalkyl group are substituted with —O—, —S—, —NH—, —N(CH$_3$)—, —C(=O)—, —OC(=O)—, or —C(=O)O—, or any one polymerizable group selected from the group consisting of groups represented by Formula Q-1 to Formula Q-5, or represents a single bond in a case where $X^{21}$ is a nitrogen atom which forms a ring structure along with $Q^{23}$ and Sp$^{23}$, and $Q^{25}$ represents a hydrogen atom, a cycloalkyl group, a group in which one or two or more —CH$_2$—'s in the cycloalkyl group are substituted with —O—, —S—, —NH—, —N(CH$_3$)—, —C(=O)—, —OC(=O)—, or —C(=O)O—, or any one polymerizable group selected from the group consisting of groups represented by Formula Q-1 to Formula Q-5, and when Sp$^{25}$ is a single bond, $Q^{25}$ is not a hydrogen atom.

It is also preferable that the polymerizable composition of the present invention contains at least one type of the polymerizable compound represented by Formula (I-21) having a structure in which a 1,4-phenylene group and a trans-1,4-cyclohexylene group alternately exist. As the polymerizable compound represented by Formula (I-21), a structure is preferable in which m21 is 2, n21 is 0, and $A^{21}$ is each of a trans-1,4-cyclohexylene group which may have a substituent and an arylene group which may have a substituent from a $Q^{21}$ side, or m21 is 1, n21 is 1, $A^{21}$ is an arylene group which may have a substituent, and $A^{22}$ is an arylene group which may have a substituent.

It is also preferable that the polymerizable composition of the present invention contains at least one type of the compound represented by Formula (I) having a partial structure represented by Formula (II).

(II)

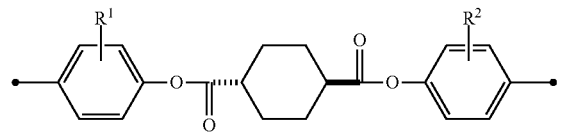

In Formula (II), a black circle represents a bonding position with the other portion of Formula (I). The partial structure represented by Formula (II) may be included as a part of a partial structure represented by Formula (III) in Formula (I).

(III)

In the formula, R$^1$ and R$^2$ are each independently a hydrogen atom or a group selected from the group consisting of an alkyl group, an alkoxy group, and a group represented by —C(=O)—X$^3$-Sp$^3$-Q$^3$. Here, X$^3$ represents a single bond, —O—, —S—, or —N(Sp$^4$-Q$^4$)—, or represents a nitrogen atom which forms a ring structure along with Q$^3$ and Sp$^3$. It is preferable that X$^3$ is a single bond or —O—. It is preferable that R$^1$ and R$^2$ are —C(=O)—X$^3$-Sp$^3$-Q$^3$. In addition, it is preferable that R$^1$ and R$^2$ are identical to each other. A bonding position of each of R$^1$ and R$^2$ with respect to a phenylene group is not particularly limited.

Sp$^3$ and Sp$^4$ each independently represent a single bond or a linking group selected from the group consisting of a linear alkylene group or a branched alkylene group having 1 to 20 carbon atoms, and a group in which one or two or more —CH$_2$—'s in the linear alkylene group or the branched alkylene group having 1 to 20 carbon atoms are substituted with —O—, —S—, —NH—, —N(CH$_3$)—, —C(=O)—, —OC(=O)—, or —C(=O)O—. It is preferable that Sp$^3$ and Sp$^4$ are each independently a linear alkylene group or a branched alkylene group having 1 to 10 carbon atoms, it is more preferable that Sp$^3$ and Sp$^4$ are each independently a linear alkylene group having 1 to 5 carbon atoms, and it is even more preferable that Sp$^3$ and Sp$^4$ are each independently a linear alkylene group having 1 to 3 carbon atoms.

Q$^3$ and Q$^4$ each independently represent a hydrogen atom, a cycloalkyl group, a group in which one or two or more —CH$_2$—'s in the cycloalkyl group are substituted with —O—, —S—, —NH—, —N(CH$_3$)—, —C(=O)—, —OC(=O)—, or —C(=O)O—, or any one polymerizable group selected from the group consisting of groups represented by Formula Q-1 to Formula Q-5.

It is also preferable that the polymerizable composition of the present invention contains at least one type of compound represented by Formula (II-2) as the compound represented by Formula (I).

(II-2)

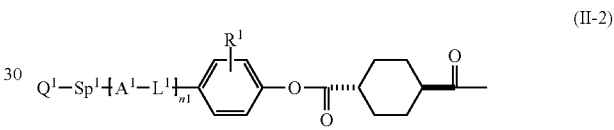

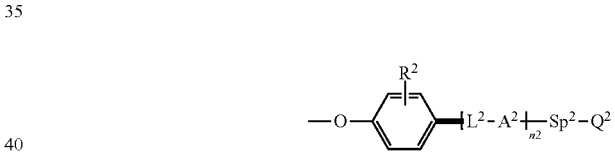

In the formula, A$^1$ and A$^2$ each independently represent a phenylene group which may have a substituent or a trans-1,4-cyclohexylene group which may have a substituent, and all of the substituents described above are each independently 1 to 4 substituents selected from the group consisting of an alkyl group, an alkoxy group, and —C(=O)—X$^3$-Sp$^3$-Q$^3$, L$^1$ and L$^2$ represent a single bond or a linking group selected from the group consisting of —CH$_2$O—, —OCH$_2$—, —(CH$_2$)$_2$OC(=O)—, —C(=O)O(CH$_2$)$_2$—, —C(=O)O—, —OC(=O)—, —OC(=O)O—, —CH=CH—C(=O)O—, and —OC(=O)—CH=CH—, and n1 and n2 each independently represent an integer of 0 to 9, and n1+n2 is less than or equal to 9.

It is also preferable that Formula (II-2) has a structure in which a phenylene group which may have a substituent and a trans-1,4-cyclohexylene group which may have a substituent (preferably unsubstituted trans-1,4-cyclohexylene group) are alternately arranged.

Hereinafter, examples of the polymerizable compound represented by Formula (I) in which 0.5<mc will be described, but the present invention is not limited thereto.

me = 0.6
1-1
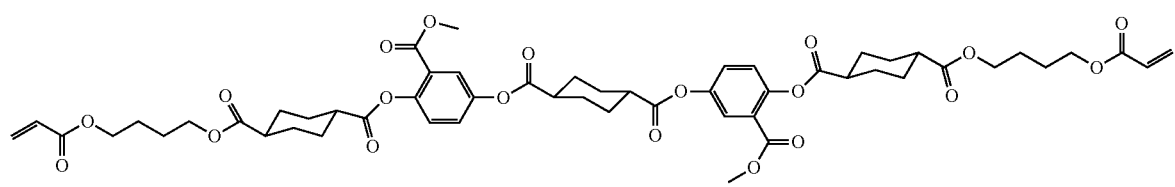
1-2
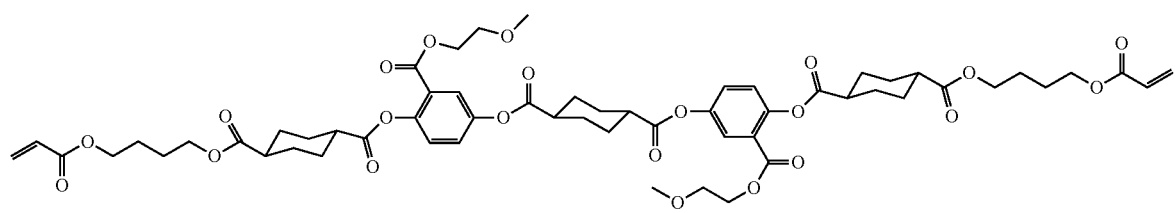
1-3
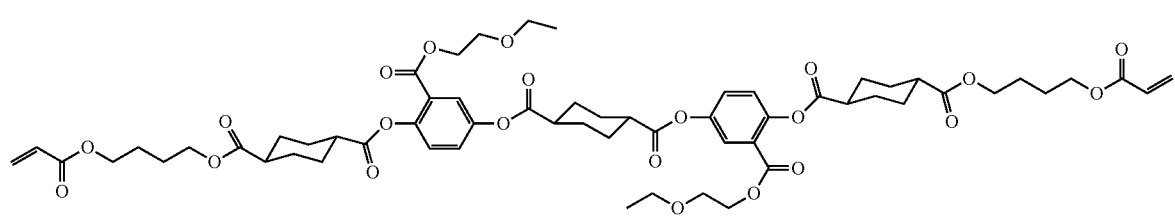
1-4
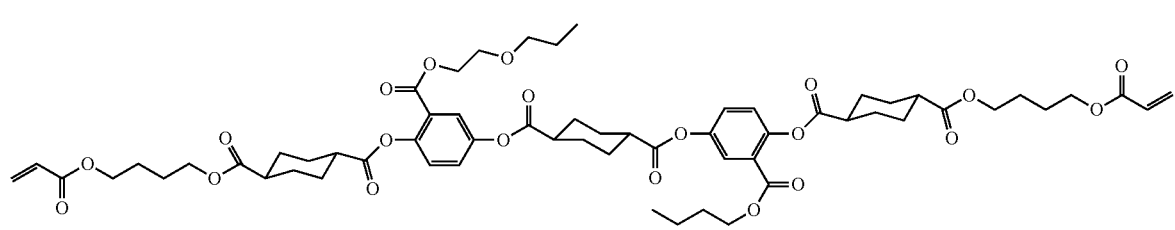
1-5
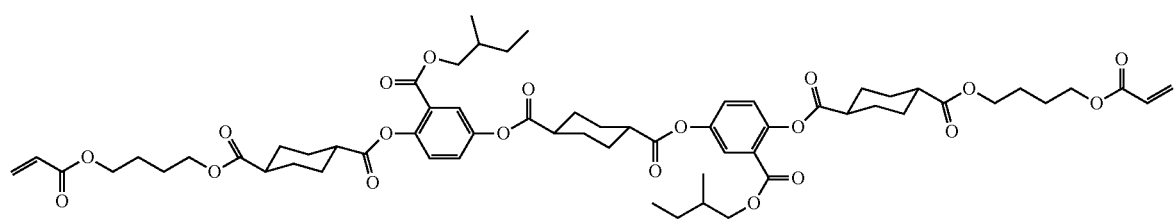
1-6
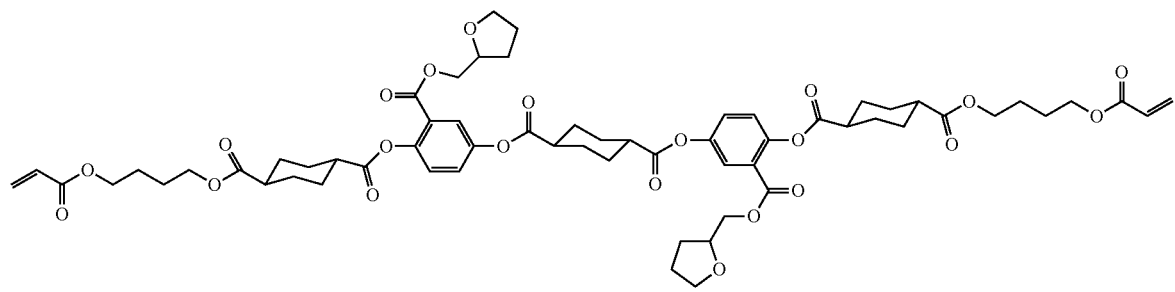

-continued
1-7
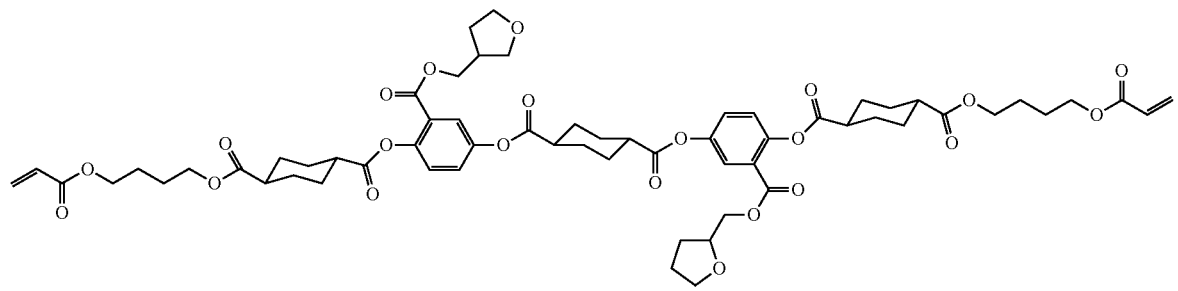
1-8
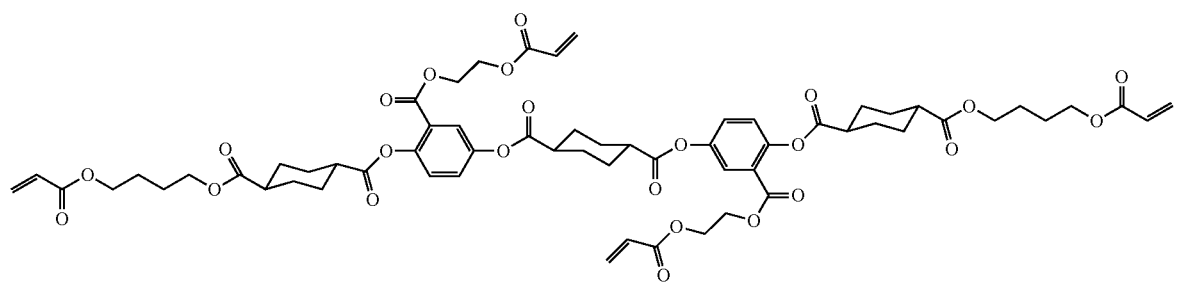
1-9
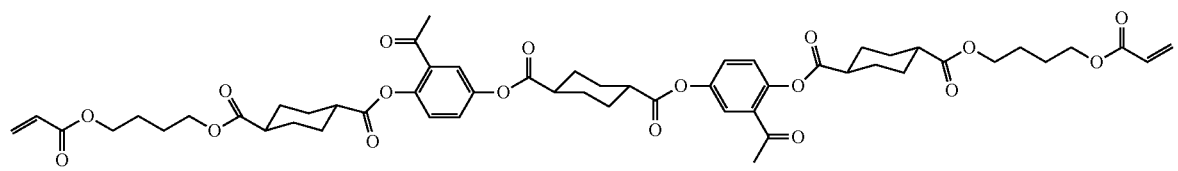
1-10
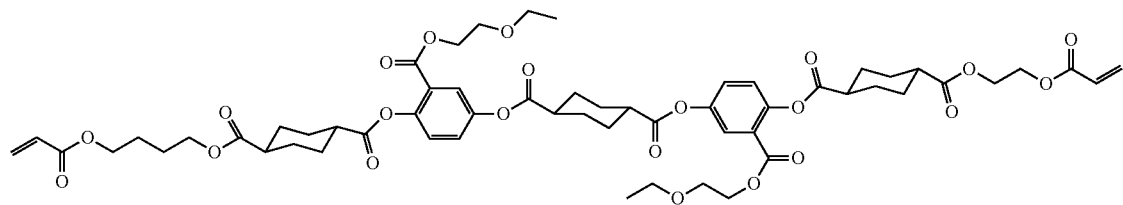
1-11
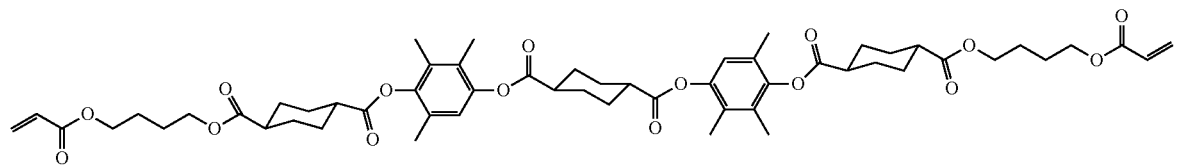
1-12
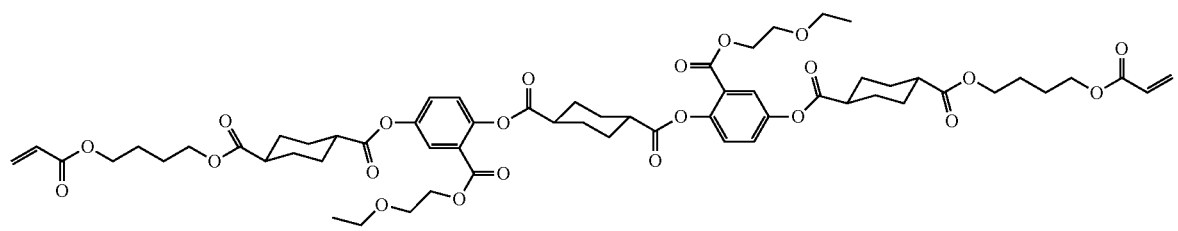

-continued
1-13
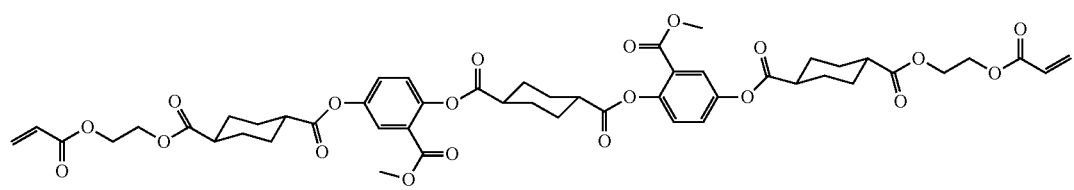
1-14
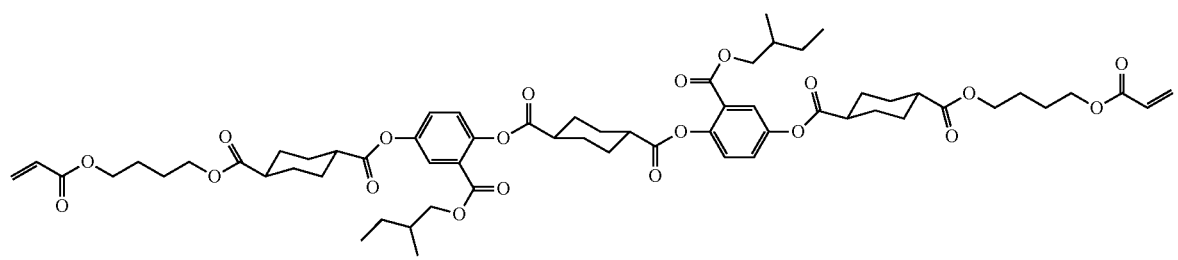
1-15
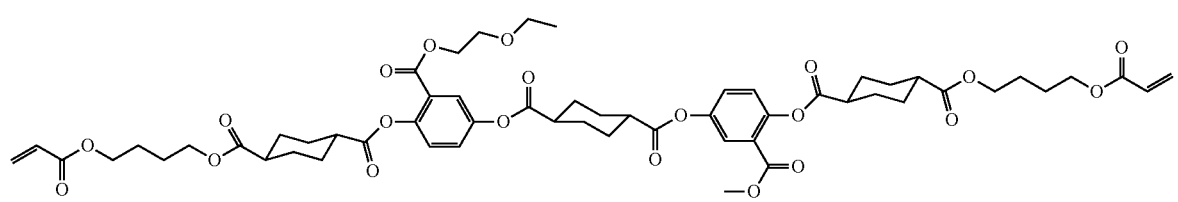
me = 0.67
1-16
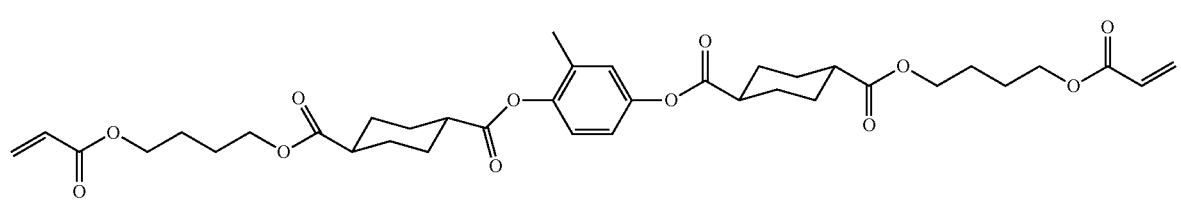
1-17
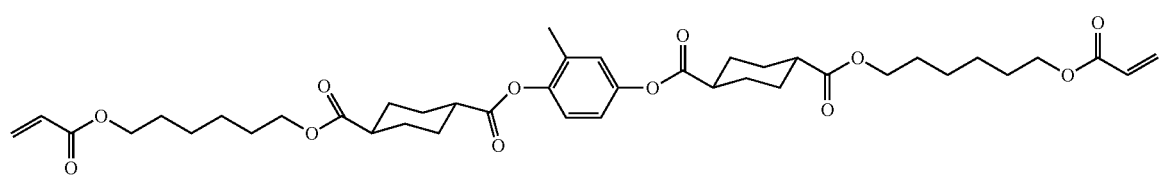
1-18
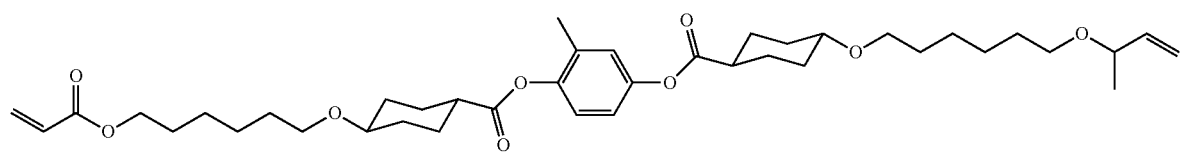
1-19
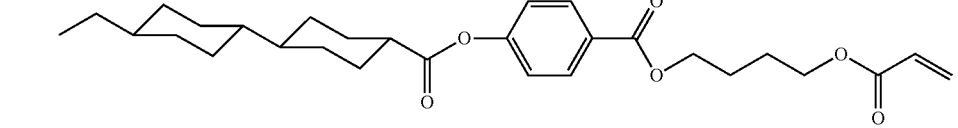
1-20
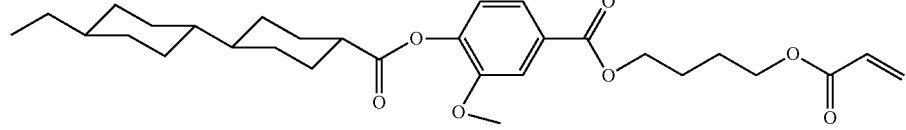

-continued
1-21
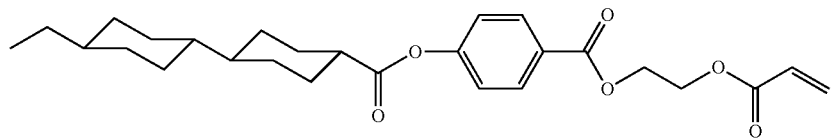
1-22
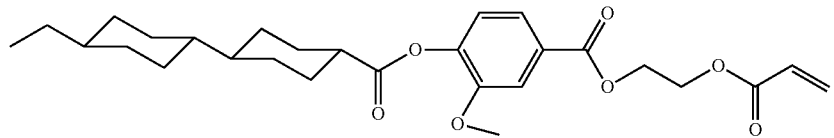
1-23
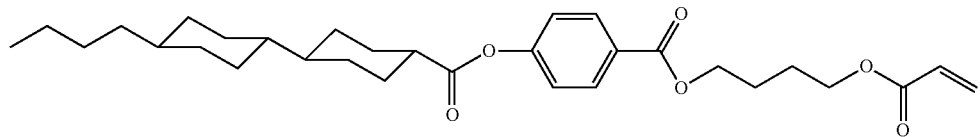
1-24
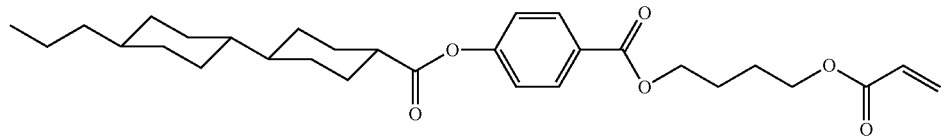
1-25
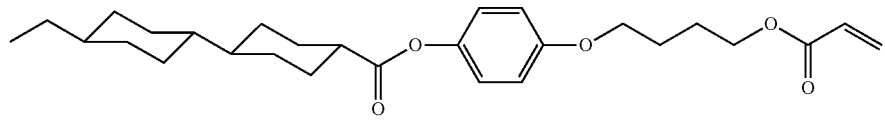
me = 0.57
1-26
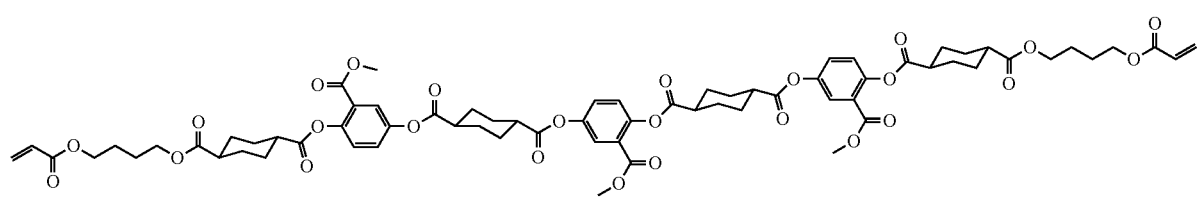
1-27
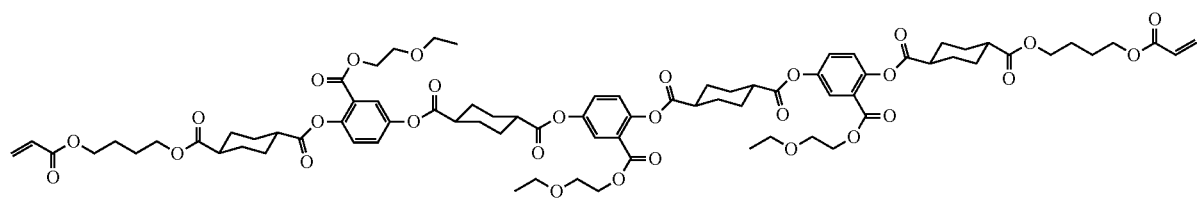
1-28
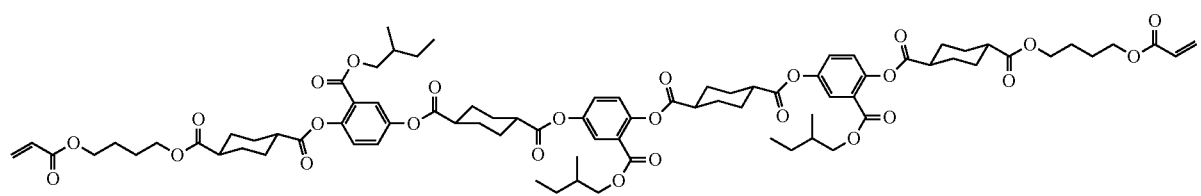

-continued
1-29
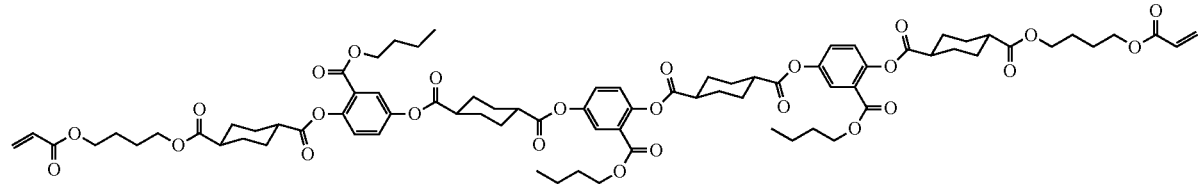
1-30
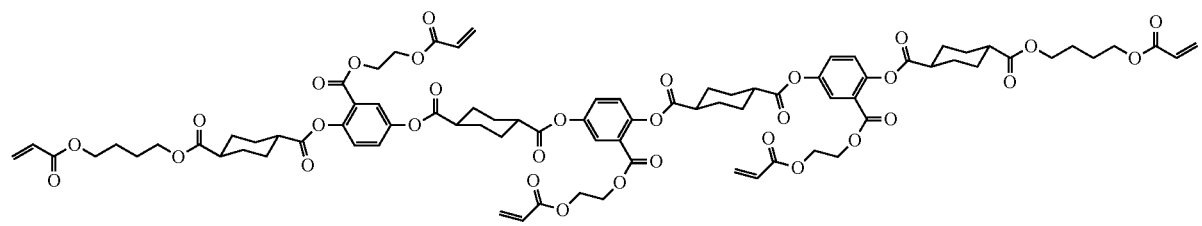
1-31
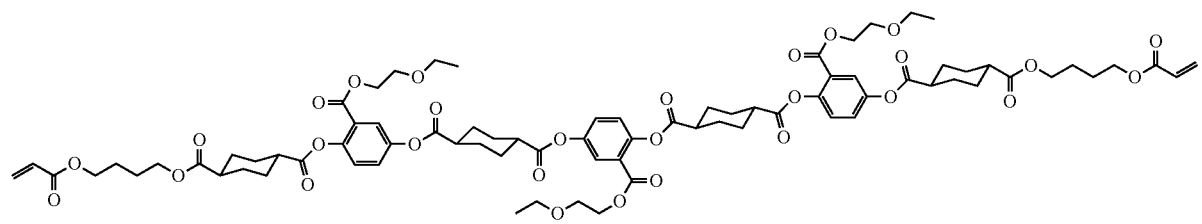
1-32
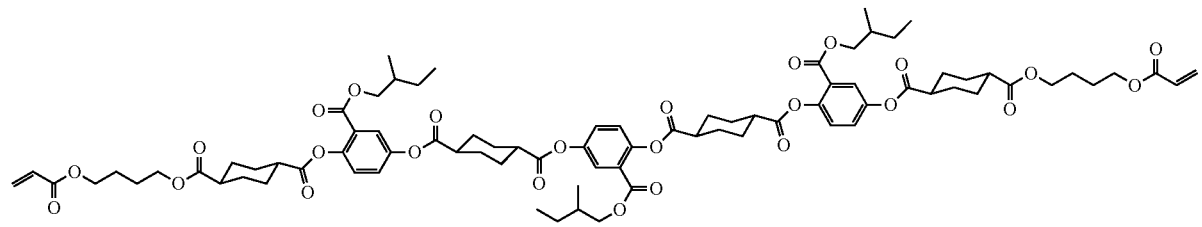
1-33
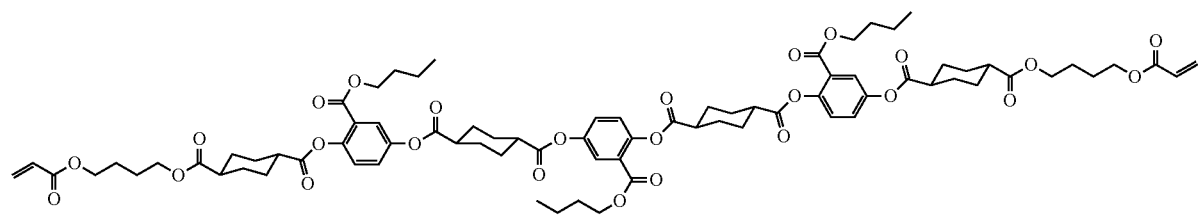
me = 0.55
1-34
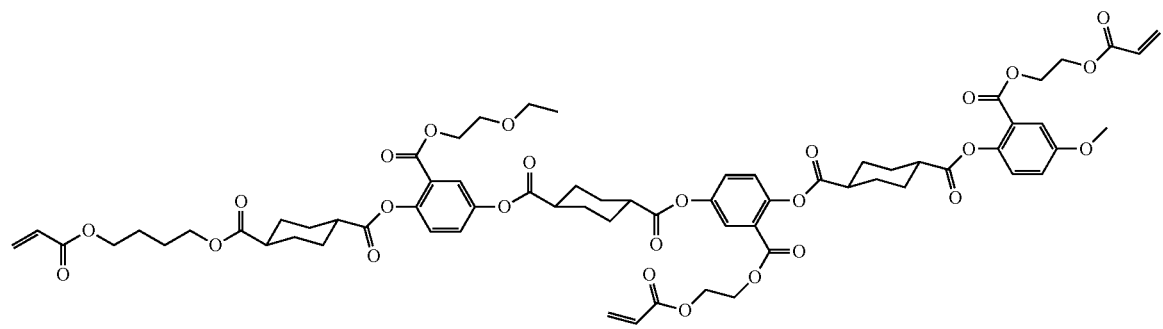

-continued
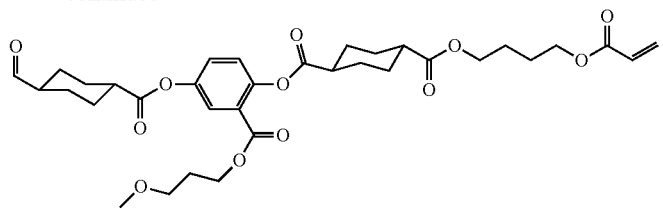
1-35
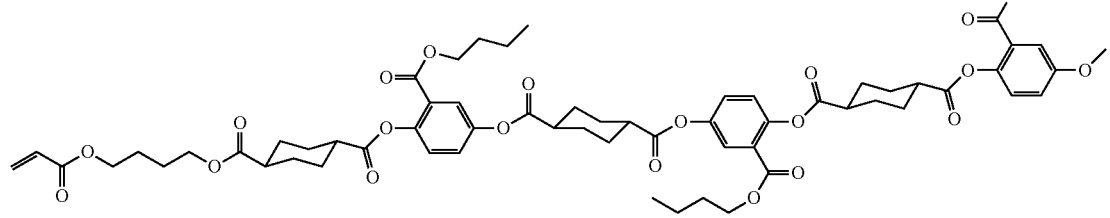
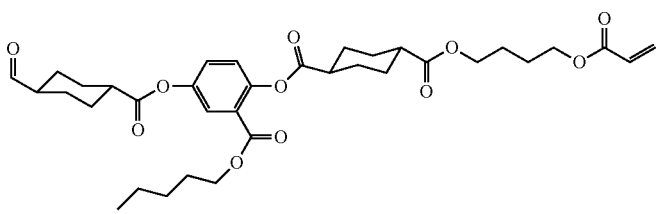
1-36
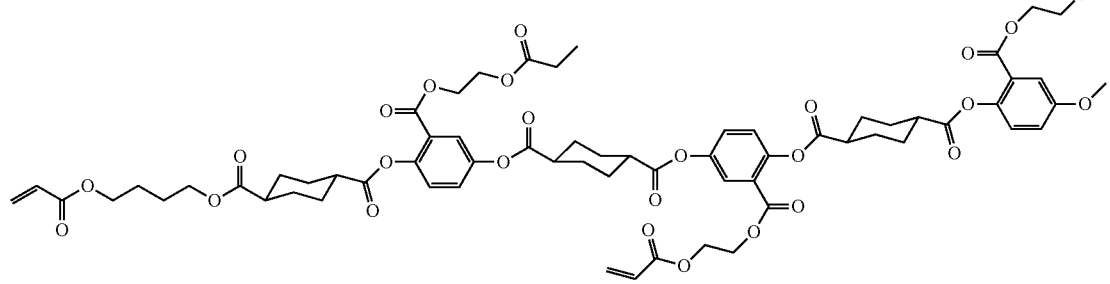
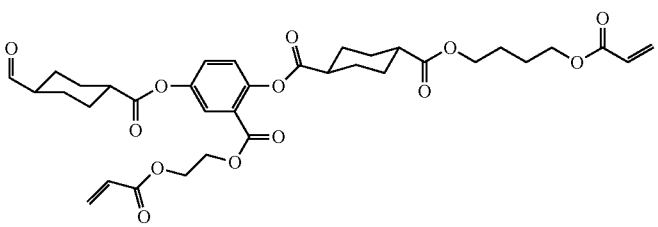
me = 0.8
56
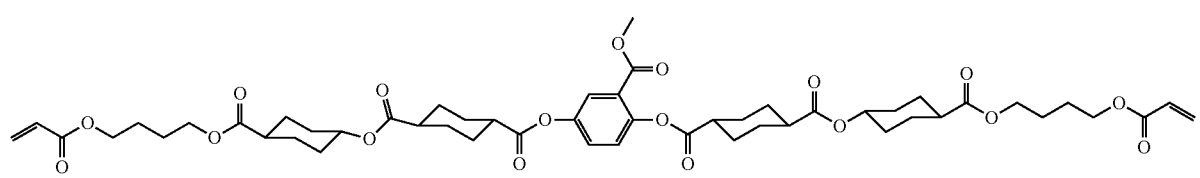
57
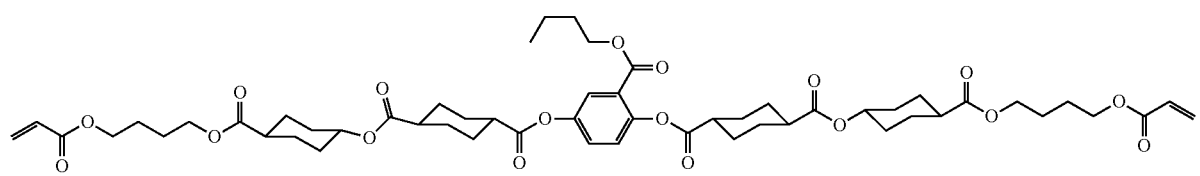

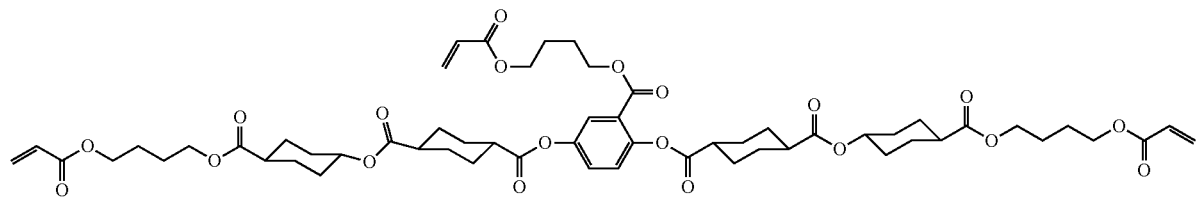

58

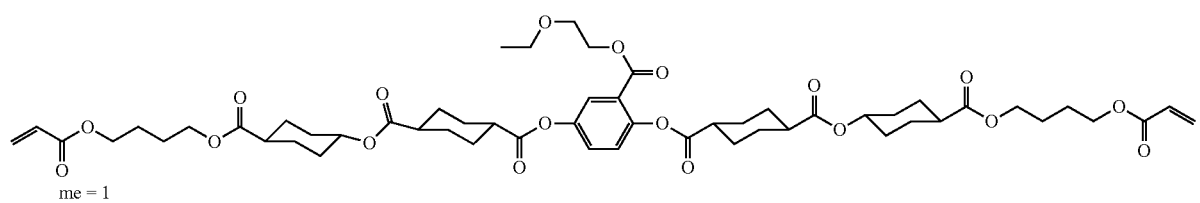

59 me = 1

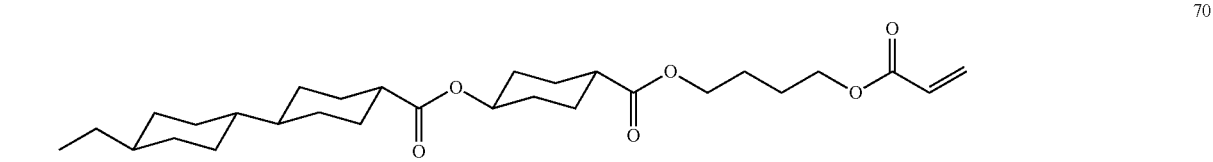

70

The polymerizable compound represented by Formula (I) can be manufactured by a known method, and for example, can be manufactured by the following method.

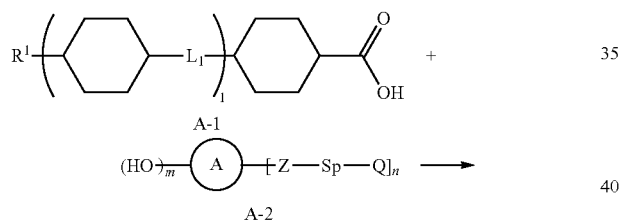

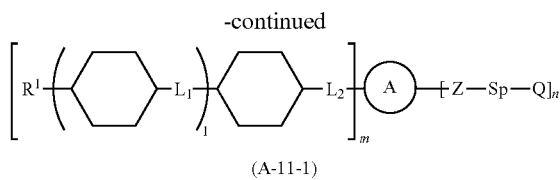

(A-11-1)

For example, in Formula (A-11-1), in a case where $L_2$ is —COO—, the polymerizable compound represented by Formula (I) can be manufactured by esterifying a carboxylic acid derivative A-1 by using a phenol (or alcohol) derivative A-2.

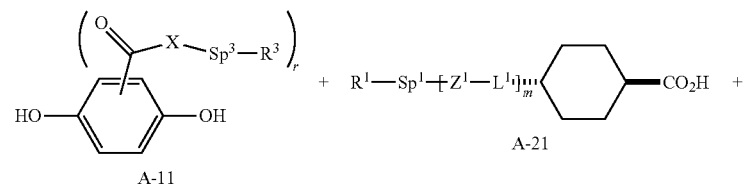

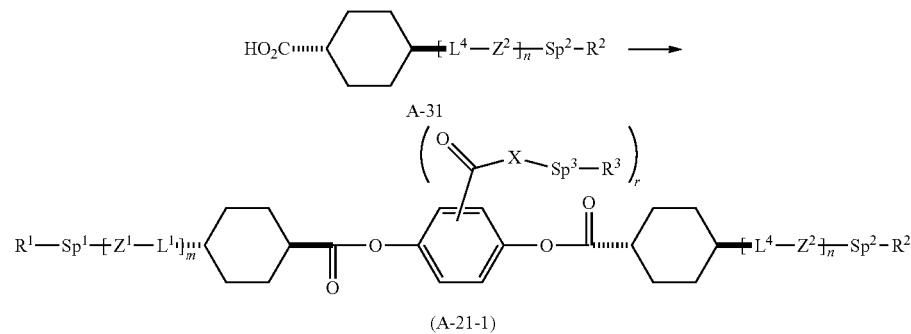

(A-21-1)

For example, in Formula (A-21-1), the polymerizable compound represented by Formula (I), can be manufactured by performing esterification by using a phenol (or alcohol) derivative A-11 and carboxylic acid derivatives A-21 and A-31.

In addition, the polymerizable compound represented by Formula (I) satisfies a plurality of properties such as being colorless and transparent, having a wide liquid crystalline phase range, being easily dissolved in a solvent, and being easily polymerized, since absorption in a visible light range is extremely low regardless of the type of substituent of an aromatic ring or a linking group. According to this, a cured film which is prepared by using a polymerizable composition containing the polymerizable compound represented by Formula (I) can satisfy a plurality of properties such as having a sufficient hardness, being colorless and transparent, having excellent weather fastness and excellent heat resistance. Accordingly, the cured film formed by using the polymerizable composition described above, for example, can be used in various applications such as a phase difference plate, a polarization element, a selective reflection film, a color filter, an antireflection film, a view angle compensation film, a holography, and an alignment film which are constituents of an optical element.

The total mass of the polymerizable compound represented by Formula (I) is may be greater than or equal to 10 mass %, is preferably 30 to 99.9 mass %, is more preferably 50 to 99.5 mass %, and is even more preferably 70 to 99 mass %, with respect to a mass of solid contents of the polymerizable composition. In particular, the polymerizable composition of the present invention preferably contains the polymerizable compound represented by Formula (I) in which mc described below satisfies 0.5<mc in the range described above, more preferably contains the polymerizable compound represented by Formula (I) in which 0.5<mc≤0.8 is satisfied in the range described above, and still more preferably contains the polymerizable compound represented by Formula (I) in which 0.5<mc<0.7 is satisfied in the range described above. Here, the total mass of the polymerizable compound represented by Formula (I) is not limited to this range.

[Combination of Polymerizable Compound Represented by Formula (I)]

Herein, in Formula (I), a number obtained by dividing the number of trans-1,4-cyclohexylene groups which may have a substituent and are represented by A by m is indicated by mc. That is, mc is a number represented by the following calculus equation.

Calculus Equation $mc$=(the number of trans-1,4-cyclohexylene groups which may have a substituent and are represented by $A$)/$m$ The polymerizable composition of the present invention contains the polymerizable compound satisfying 0.5<mc<0.7 and the polymerizable compound satisfying 0.5<mc. Herein, the two types of the polymerizable compounds represented by Formula (I) in which mc's are different from each other mean two types: the polymerizable compound represented by Formula (I) in which mc satisfies 0.5<mc; and the polymerizable compound represented by Formula (I) in which mc satisfies 0.5<mc<0.7. However, the polymerizable composition of the present invention may contain the polymerizable compound represented by Formula (I) in which mc is less than or equal to 0.5.

The polymerizable composition of the present invention contains at least two types of the polymerizable compounds represented by Formula (I) in which mc's are different from each other. At least one of the two types of the polymerizable compounds satisfies 0.5<mc<0.7, and at least the other thereof satisfies 0.5<mc. In the polymerizable composition of the present invention, it is preferable that at least one of the two types of the polymerizable compounds satisfies 0.5<mc<0.65. Moreover, it is preferable that one of the two types of the polymerizable compounds satisfies 0.5<mc<0.7, and the other satisfies 0.5<mc≤0.8, it is more preferable that both of the two types of the polymerizable compounds satisfies 0.5<mc<0.7, and it is still more preferable that both of the two types of the polymerizable compounds satisfies 0.5<mc<0.65.

The polymerizable composition of the present invention contains the polymerizable compound represented by Formula (I) in a combination as described above, and thus, has low birefringence (for example, birefringence obtained from a phase difference and a film thickness of a layer obtained by polymerizing a liquid crystal layer in a monoaxial alignment state described in an example at 50° C. is 0.040 to 0.110) and excellent liquid crystallinity. That is, in a range in which excellent liquid crystallinity is exhibited, the birefringence can be adjusted in a range of a comparatively low value. In addition, even when the polymerizable composition contains a solvent which is generally used for preparing a film, the polymerizable compound is rarely precipitated. In a case where a film is formed by using the polymerizable composition of the present invention, cissing rarely occurs, and a film shape also tends to be rarely disturbed. In addition, a cholesteric liquid crystalline phase is formed by using the polymerizable composition of the present invention, a film is formed by immobilizing the cholesteric liquid crystalline phase, and thus, it is possible to obtain a reflection film having a narrow wavelength range of selective reflection, that is, a reflection film having high selectivity in a reflection wavelength range.

Specifically, mc is calculated as described below, according to the total number of cyclic divalent groups represented by A in the polymerizable compound represented by Formula (I), that is, m, and in the equation, the number of trans-1,4-cyclohexylene groups which may have a substituent and are represented by A in the polymerizable compound represented by Formula (I) (hereinafter, may be referred to as the number of cyclohexanes). Hereinafter, a compound in which m represents 3 to 9 will be described as an example.

TABLE 1

| m | Number of Cyclohexanes | mc | |
|---|---|---|---|
| 3 | 3 | 1 | |
| 3 | 2 | 0.67 | Gr. 1 |
| 4 | 4 | 1 | |
| 4 | 3 | 0.75 | |
| 5 | 5 | 1 | |
| 5 | 4 | 0.80 | |
| 5 | 3 | 0.60 | Gr. 1 |
| 6 | 5 | 0.83 | |
| 6 | 4 | 0.67 | Gr. 1 |
| 7 | 6 | 0.86 | |
| 7 | 5 | 0.71 | |
| 7 | 4 | 0.57 | Gr. 1 |
| 8 | 7 | 0.88 | |
| 8 | 6 | 0.75 | |
| 8 | 5 | 0.63 | Gr. 1 |
| 9 | 7 | 0.78 | |
| 9 | 6 | 0.67 | Gr. 1 |
| 9 | 5 | 0.56 | Gr. 1 |

Gr. 1: 0.5 < mc < 0.7 is satisfied

The polymerizable composition of the present invention may contain, for example, at least one type of Gr.1 in Table 1 described above and one type of compound which has different mc from that of the one type of Gr.1 and is shown in Table 1 described above.

contained in the polymerizable composition of the present invention are different from each other.

It is also preferable that the polymerizable composition of the present invention, for example, contains at least two types of compounds represented by Formula (V).

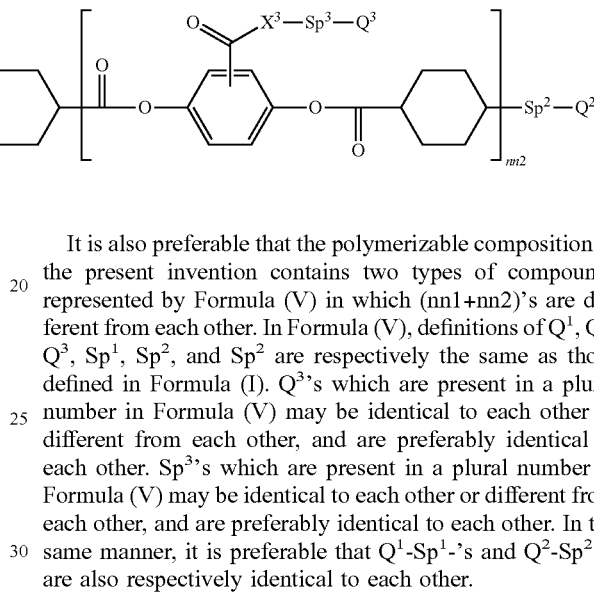

(V)

It is preferable that the polymerizable composition of the present invention contains a combination of the polymerizable compounds represented by Formula (I) in which mc is as follows:
a combination of mc=0.67 and mc=1;
a combination of mc=0.67 and mc=0.80;
a combination of mc=0.67 and mc=0.75;
a combination of mc=0.67 and mc=0.71;
a combination of mc=0.67 and mc=0.60;
a combination of mc=0.67 and mc=0.57;
a combination of mc=0.67 and mc=0.56;
a combination of mc=0.60 and mc=1;
a combination of mc=0.60 and mc=0.80;
a combination of mc=0.60 and mc=0.57;
a combination of mc=0.60 and mc=0.56;
a combination of mc=0.57 and mc=0.56;
a combination of mc=0.67, mc=0.60, and mc=0.57;
a combination of mc=0.60, mc=0.57, and mc=0.56; and
a combination of mc=0.67, mc=0.60, mc=0.57, and mc=0.56.

Among them, the followings are particularly preferable:
a combination of mc=0.67 and mc=0.60;
a combination of mc=0.60 and mc=1;
a combination of mc=0.60 and mc=0.80;
a combination of mc=0.60 and mc=0.57; and
a combination of mc=0.60 and mc=0.56.

Examples of a combination of m's in the polymerizable compounds which are represented by Formula (I) in which mc's are different from each other and are contained in the polymerizable composition of the present invention include the followings:
a combination of m=3 and m=3;
a combination of m=5 and m=5;
a combination of m=3 and m=5;
a combination of m=3 and m=7;
a combination of m=3 and m=9;
a combination of m=5 and m=7;
a combination of m=5 and m=9;
a combination of m=7 and m=9;
a combination of m=3, m=5, and m=7;
a combination of m=5, m=7, and m=9; and
a combination of m=3, m=5, m=7, and m=9.

Among them, the followings are particularly preferable:
a combination of m=3 and m=5;
a combination of m=5 and m=7; and
a combination of m=5 and m=9.

It is also preferable that m's in at least two types of the polymerizable compounds which are represented by Formula (I) in which mc's are different from each other and are It is also preferable that the polymerizable composition of the present invention contains two types of compounds represented by Formula (V) in which (nn1+nn2)'s are different from each other. In Formula (V), definitions of $Q^1$, $Q^2$, $Q^3$, $Sp^1$, $Sp^2$, and $Sp^2$ are respectively the same as those defined in Formula (I). $Q^3$'s which are present in a plural number in Formula (V) may be identical to each other or different from each other, and are preferably identical to each other. $Sp^3$'s which are present in a plural number in Formula (V) may be identical to each other or different from each other, and are preferably identical to each other. In the same manner, it is preferable that $Q^1$-$Sp^1$-'s and $Q^2$-$Sp^2$-'s are also respectively identical to each other.

In the formula, nn1 and nn2 each independently represent an integer of 1 or 2.

For example, a polymerizable composition containing at least a compound in which nn1+nn2 is 2 and a compound in which nn1+nn2 is 3, a polymerizable composition containing at least a compound in which nn1+nn2 is 2 and a compound in which nn1+nn2 is 4, a polymerizable composition containing at least a compound in which nn1+nn2 is 3 and a compound in which nn1+nn2 is 4, and a polymerizable composition containing a compound in which nn1+nn2 is 2, a compound in which nn1+nn2 is 3, and a compound in which nn1+nn2 is 4 are preferable.

It is also preferable that the polymerizable composition of the present invention contains at least one type of the polymerizable compound represented by Formula (I) in which m represents an integer of 6 to 12. The polymerizable compound represented by Formula (I) in which m represents an integer of 6 to 12 shows an effect of exhibiting a liquid crystalline phase in a wide temperature range by increasing a phase transition temperature of a liquid crystal composition. It is more preferable that the polymerizable composition of the present invention contains at least one type of the polymerizable compound represented by Formula (I) in which m represents 7 or 9. Preferred examples of the polymerizable compound represented by Formula (I) in which m represents 7 or 9 include a compound represented by Formula (II-2) in which n1+n2 is 3 to 6. Particularly preferred examples thereof include a compound represented by Formula (V) in which a value represented by nn1+nn2 is 3 or 4.

A content ratio of two types of the polymerizable compounds represented by Formula (I) in the polymerizable composition of the present invention is not particularly limited, but a mass ratio of the polymerizable compounds may be 95:5 to 5:95 and is preferably 90:10 to 10:90.

It is also preferable that the two types of the polymerizable compounds represented by Formula (I) in the polymerizable composition of the present invention are compounds simultaneously obtained in a synthesizing process.

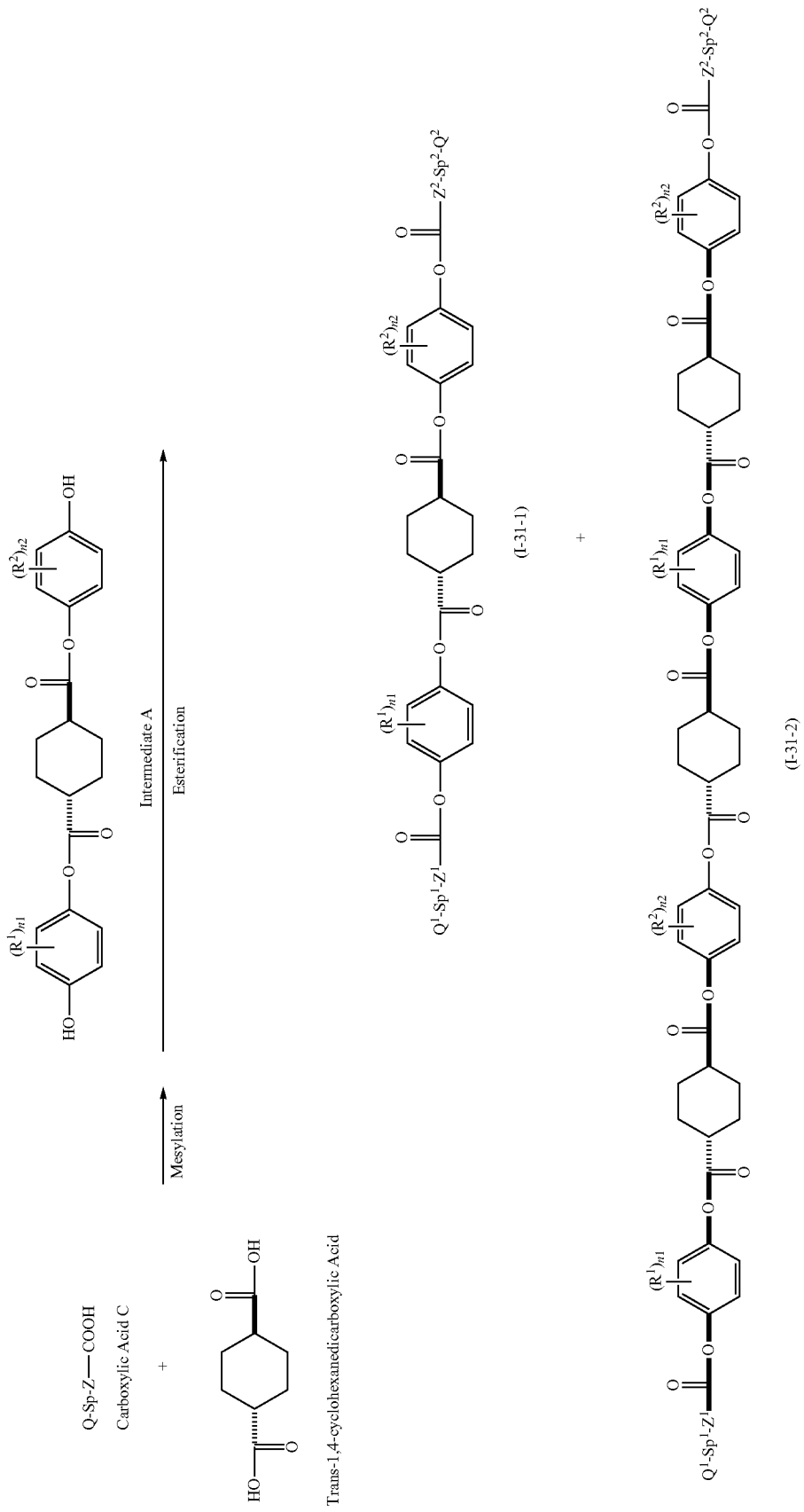

Examples of a method of simultaneously manufacturing a polymerizable compound represented by Formula (I-31-1) and a polymerizable compound represented by Formula (I-31-2) include a method of mixing a carboxylic acid C with a small amount of trans-1,4-cyclohexane dicarboxylic acid and esterifying the mixture and an intermediate A.

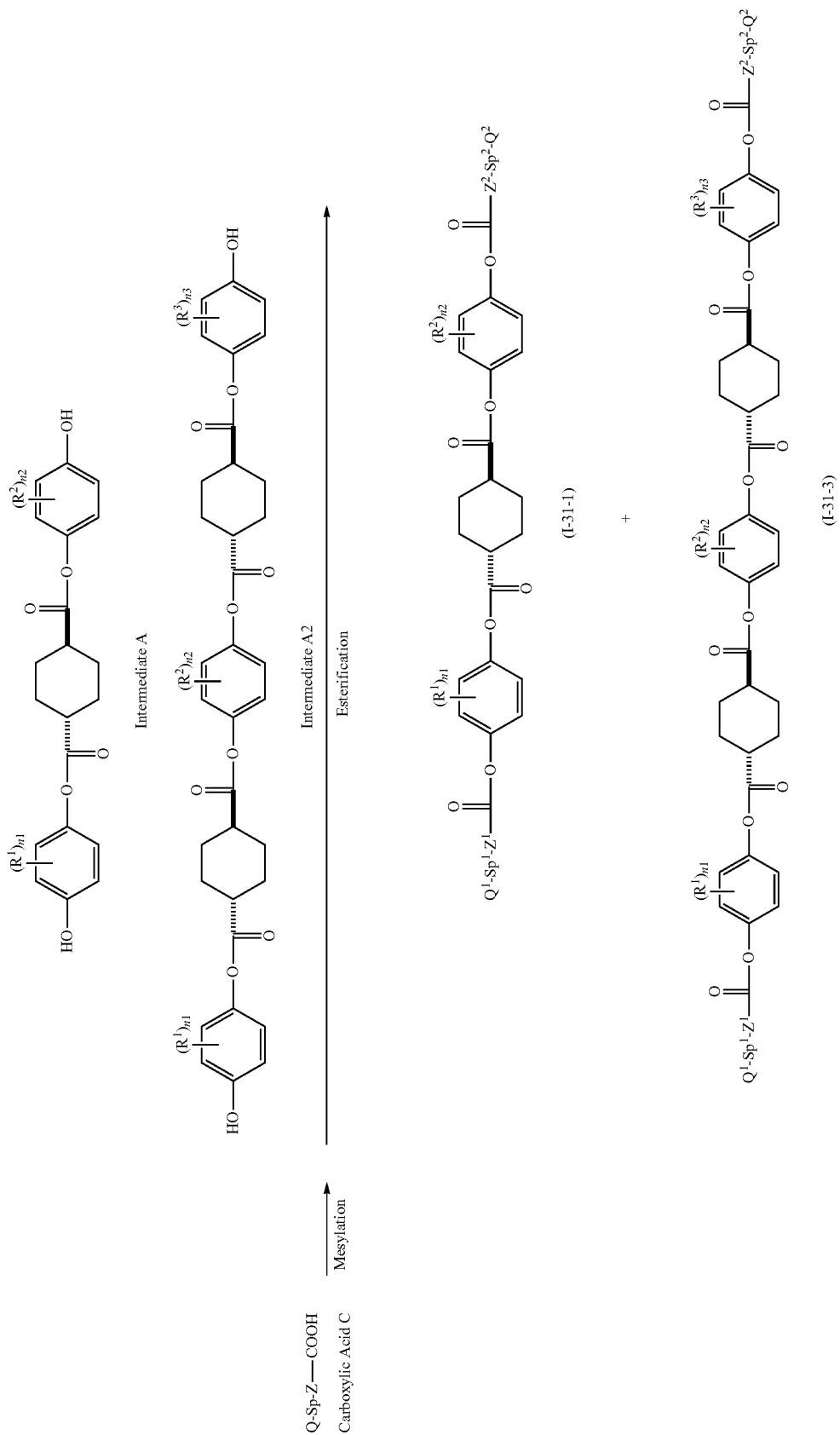

As other examples, examples of a method of simultaneously manufacturing the polymerizable compound represented by Formula (I-31-1) and a polymerizable compound represented by Formula (I-31-3) include a method of esterifying the carboxylic acid C and the intermediate A and an intermediate A-2.

Examples of an esterification method include a method of allowing an activated carboxylic acid and a phenol (or alcohol) derivative to act in the presence of a base, and a method of directly esterifying a carboxylic acid and a phenol (or alcohol) derivative by using a condensation agent such as carbodiimide. A method of activating a carboxylic acid is more preferable from the viewpoint of a by-product.

An activation method of a carboxylic acid includes acid chlorination using thionyl chloride, oxalyl chloride, or the like, and a method of allowing a carboxylic acid and mesyl chloride to act to prepare a mixed acid anhydride.

[Other Liquid Crystal Compounds]

The polymerizable composition may contain one or more other liquid crystal compounds along with the polymerizable compound represented by Formula (I). The polymerizable compound represented by Formula (I) has high compatibility with respect to the other liquid crystal compounds, and thus, even in a case of being mixed with the other liquid crystal compounds, it is possible to form a film having high transparency without the occurrence of opacification or the like. The other liquid crystal compounds can be used together, and thus, it is possible to provide compositions having various compositions suitable for various applications. Examples of the other liquid crystal compounds which can be used together include a rod-like nematic liquid crystal compound. Examples of the rod-like nematic liquid crystal compound include azomethines, azoxies, cyanobiphenyls, cyanophenyl esters, benzoic acid esters, phenyl cyclohexane carboxylic acid esters, cyanophenyl cyclohexanes, cyano-substituted phenyl pyrimidines, alkoxy-substituted phenyl pyrimidines, phenyl dioxanes, tolans, and alkenyl cyclohexyl benzonitriles. It is possible to use not only a low molecular liquid crystal compound but also a high molecular liquid crystal compound.

The other liquid crystal compounds may be a polymerizable liquid crystal compound or a non-polymerizable liquid crystal compound. A rod-like liquid crystal compound not having a polymerizable group is described in various literatures (for example, Y. Goto et. al., Mol. Cryst. Liq. Cryst. 1995, Vol. 260, pp. 23-28).

A polymerizable rod-like liquid crystal compound can be obtained by introducing a polymerizable group into a rod-like liquid crystal compound. Examples of the polymerizable group include an unsaturated polymerizable group, an epoxy group, and an aziridinyl group, and among them, the unsaturated polymerizable group is preferable, and an ethylenically unsaturated polymerizable group is particularly preferable. The polymerizable group can be introduced into the molecules of the rod-like liquid crystal compound by various methods. The number of polymerizable groups in the polymerizable rod-like liquid crystal compound is preferably 1 to 6, and is more preferably 1 to 3. Examples of the polymerizable rod-like liquid crystal compound include compounds described in Makromol. Chem., Vol. 190, p. 2255 (1989), Advanced Materials Vol. 5, p. 107 (1993), the specification of U.S. Pat. No. 4,683,327A, the specification of U.S. Pat. No. 5,622,648A, the specification of U.S. Pat. No. 5,770,107A, WO95/22586A, WO95/24455A, WO97/00600A, WO98/23580A, WO98/52905A, JP1989-272551A (JP-H01-272551A), JP1994-16616A (JP-H06-16616A), JP1995-110469A (JP-H07-110469A), JP1999-80081A (JP-H11-80081A), JP2001-328973A, and the like. Two or more types of polymerizable rod-like liquid crystal compounds may be used together. In a case where two or more types of polymerizable rod-like liquid crystal compounds are used together, it is possible to decrease an alignment temperature.

The added amount of the other liquid crystal compounds is not particularly limited, but is preferably 0 to 70 mass %, is more preferably 0 to 50 mass %, and is even more preferably 0 to 30 mass %, with respect to the mass of solid contents of the polymerizable composition. However, the added amount of the other liquid crystal compounds is not limited to the range described above. In the polymerizable composition, a mass ratio of the polymerizable compound represented by Formula (I) to the other liquid crystal compounds (Mass of Polymerizable Compound represented by Formula (I)/Mass of Other Liquid Crystal Compounds) may be 100/0 to 30/70, is preferably 100/0 to 50/50, and is more preferably 100/0 to 70/30. The ratio can be adjusted to be in a preferred range according to the application.

[Chiral Compound]

The polymerizable composition may contain a chiral compound. By using the chiral compound, it is possible to prepare the polymerizable composition as a composition having a cholesteric liquid crystalline phase. The chiral compound may be a liquid crystalline chiral compound, or may be a non-liquid crystalline chiral compound. As the chiral compound, various known compounds are used. Examples of chiral agents include compounds described in Liquid Crystal Device Handbook (Chap. 3, Sec. 4-3, Chiral Agent for TN and STN, p. 199, Japan Society for the Promotion of Science, edited by The 142-nd Committee, 1989), JP2003-287623A, JP2002-302487A, JP2002-80478A, JP2002-80851A, JP2010-181852, and JP2014-034581A.

In general, the chiral compound has an asymmetric carbon atom, and an axially asymmetric compound or a planarly asymmetric compound which does not has an asymmetric carbon atom can be used. Examples of the axially asymmetric compound or the planarly asymmetric compound include binaphthyl, helicene, paracyclophane, and derivatives thereof. The chiral compound (a chiral agent) may have a polymerizable group. In a case where the chiral compound has a polymerizable group, and the rod-like liquid crystal compound to be used together also has a polymerizable group, it is possible to form a polymer having a repeating unit derived from the rod-like liquid crystal compound and a repeating unit derived from the chiral compound by a polymerization reaction between a polymerizable chiral compound and a polymerizable rod-like liquid crystal compound. Therefore, the polymerizable group in the polymerizable chiral compound is a polymerizable rod-like liquid crystal compound, and in particular, is preferably a group identical to the polymerizable group in the polymerizable compound represented by Formula (I). Accordingly, the polymerizable group of the chiral compound is preferably an unsaturated polymerizable group, an epoxy group, or an aziridinyl group, is more preferably an unsaturated polymerizable group, and is particularly preferably an ethylenically unsaturated polymerizable group.

In the polymerizable composition, it is preferable that the content of the chiral compound is 0.5 to 30 mass % with respect to a liquid crystal compound containing the polymerizable compound represented by Formula (I).

It is preferable that a use amount of the chiral compound is small since a small amount of chiral compound does not tend to affect liquid crystallinity. Accordingly, a compound which has a strong twisting force such that twisted alignment at a desired spiral pitch can be attained even in a case where a small amount of chiral compound is used is preferable as the chiral compound. Examples of such a chiral agent having a strong twisting force include a chiral agent described in JP2003-287623A. In addition, chiral agents described in JP2002-302487A, JP2002-80478A, JP2002-80851A, and JP2014-034581A are included. As the chiral agent, an isosorbide derivative, an isomannide derivative, and a binaphthyl derivative can be preferably used. As the isosorbide derivative, commercially available products such as LC-756 manufactured by BASF SE may be used.

A film formed by setting the polymerizable composition containing the chiral compound to a cholesteric liquid crystalline phase, and then by immobilizing the cholesteric liquid crystalline phase has selective reflection properties with respect to light at a predetermined wavelength according to a spiral pitch, and is useful as a reflection film (for example, a visible light reflection film or an infrared ray reflection film). By using the polymerizable compound represented by Formula (I) which has low birefringence, there is an advantage in that a reflection wavelength range becomes narrower, and selectivity becomes higher, compared to a film having the same thickness in which a liquid crystal compound having higher birefringence is used.

[Polymerization Initiator]

It is preferable that the polymerizable composition contains a polymerization initiator. For example, in an aspect where a cured film is formed by performing a curing reaction by ultraviolet ray irradiation, it is preferable that a polymerization initiator to be used is a photopolymerization initiator which can initiate a polymerization reaction by ultraviolet ray irradiation. Examples of the photopolymerization initiator include an α-carbonyl compound (described in the specification of each of U.S. Pat. Nos. 2,367,661A and 2,367,670A), acyloin ether (described in the specification of U.S. Pat. No. 2,448,828A), an α-hydrocarbon-substituted aromatic acyloin compound (described in the specification of U.S. Pat. No. 2,722,512A), a polynuclear quinone compound (described in the specification of each of U.S. Pat. Nos. 3,046,127A and 2,951,758A), a combination between a triaryl imidazole dimer and p-aminophenyl ketone (described in the specification of U.S. Pat. No. 3,549,367A), an acridine compound and a phenazine compound (described in JP1985-105667A (JP-S60-105667A) and in the specification of U.S. Pat. No. 4,239,850A), an acylphosphineoxide compound (described in JP1988-40799B (JP-S63-40799B), JP1993-29234B (JP-H05-29234B), JP1998-95788B (JP-H10-95788B), and JP1998-29997B (JP-H10-29997B)), an oxime compound (described in JP1988-40799B (JP-S63-40799B), JP1993-29234B (JP-H05-29234B), JP1998-95788B (JP-H10-95788B), JP1998-29997B (JP-H10-29997B), JP2001-233842A, JP2000-80068A, JP2006-342166A, JP2013-114249A, JP2014-137466A, JP4223071B, JP2010-262028A, and JP2014-500852A), and an oxadiazole compound (described in the specification of US4212970A), and the like.

It is also preferable that the acylphosphineoxide compound and the oxime compound are used as the polymerization initiator.

As the acylphosphineoxide compound, it is possible to use IRGACURE819 manufactured by BASF Japan Ltd. (compound name: bis(2,4,6-trimethylbenzoyl)-phenylphosphineoxide) which is a commercially available product. As the oxime compound, it is possible to use IRGACURE OXE01 (manufactured by BASF SE), IRGACURE OXE02 (manufactured by BASF SE), TR-PBG-304 (manufactured by Changzhou Tronly New Electronic Materials Co., Ltd.), ADEKA ARKLS NCI-930 (manufactured by ADEKA CORPORATION), and ADEKA ARKLS NCI-831 (manufactured by ADEKA CORPORATION) which are commercially available products.

Only one type of polymerization initiator may be used, or two or more types of polymerization initiators may be used together.

The content of the photopolymerization initiator in the polymerizable composition is preferably 0.1 to 20 mass %, and is more preferably 1 to 8 mass %, with respect to the mass of solid contents of the polymerizable composition.

[Alignment Control Agent]

An alignment control agent which contributes to stable or prompt formation of a liquid crystalline phase (for example, a cholesteric liquid crystalline phase) may be added to the polymerizable composition. Examples of the alignment control agent include a fluorine-containing (meth)acrylate-based polymer, compounds represented by General Formulas (X1) to (X3) described in WO2011/162291A, and a compound described in paragraphs [0020] to [0031] of JP2013-47204A. The polymerizable composition may contain two or more types of compounds selected from the compounds described above. The compounds can reduce tilt angles of the molecules of the liquid crystal compound or substantially horizontally align the tilt angles in an air interface of a layer. Furthermore, herein, "horizontal alignment" indicates that a major axis of a liquid crystal molecule is parallel to a surface of a film, but does not indicate that the major axis of the liquid crystal molecule is required to be exactly parallel to the surface of the film, and herein, the "horizontal alignment" indicates alignment in which a tilt angle with respect to a horizontal surface is less than 20 degrees. In a case where the liquid crystal compound is horizontally aligned in the vicinity of the air interface, an alignment defect rarely occurs, and thus, transparency in a visible light range increases. In contrast, in a case where the molecules of the liquid crystal compound are aligned at a large tilt angle, for example, the liquid crystal compound is set to a cholesteric liquid crystalline phase, this is not preferable since a spiral axis thereof is shifted from a normal direction of the surface of the film, and thus, reflectivity decreases or a fingerprint pattern is generated, and haze increases or diffraction properties are exhibited.

Examples of the fluorine-containing (meth)acrylate-based polymer which can be used as the alignment control agent are described in [0018] to [0043] of JP2007-272185A, and the like.

One type of compound may be independently used, or two or more types of compounds may be used together, as the alignment control agent.

The content of the alignment control agent in the polymerizable composition is preferably 0.01 to 10 mass %, is more preferably 0.01 to 5 mass %, and is particularly preferably 0.02 to 1 mass %, with respect to the mass of the compound represented by Formula (I).

[Cross-Linking Agent]

The polymerizable composition may arbitrarily contain a cross-linking agent in order to improve film hardness after being cured and to improve durability. A cross-linking agent which is cured by an ultraviolet ray, heat, humidity, and the like can be suitably used as the cross-linking agent.

The cross-linking agent is not particularly limited, but can be suitably selected according to the purpose, and examples of the cross-linking agent include a polyfunctional acrylate compound such as trimethylol propane tri(meth)acrylate, pentaerythritol tri(meth)acrylate, and pentaerythritol tetraacrylate; an epoxy compound such as glycidyl (meth)

acrylate and ethylene glycol diglycidyl ether; an aziridine compound such as 2,2-bishydroxy methyl butanol-tris[3-(1-aziridinyl) propionate] and 4,4-bis(ethylene iminocarbonyl amino) diphenyl methane; an isocyanate compound such as hexamethylene diisocyanate and biuret type isocyanate; a polyoxazoline compound having an oxazoline group in a side chain; an alkoxy silane compound such as vinyl trimethoxy silane and N-(2-aminoethyl)3-aminopropyl trimethoxy silane, and the like. In addition, a known catalyst can be used according to the reactivity of the cross-linking agent, and thus, productivity can be improved in addition to the improvement in the film hardness and the durability. One type of the compound may be independently used, or two or more types thereof may be used together.

The content of the cross-linking agent is preferably 3 mass % to 20 mass %, and is more preferably 5 mass % to 15 mass %, with respect to the mass of solid contents of the polymerizable composition. In a case where the content of the cross-linking agent is greater than or equal to 3 mass %, a cross-linking density improvement effect further increases, and in a case where the content of the cross-linking agent is less than or equal to 20 mass %, stability of a cholesteric liquid crystal layer becomes higher.

[Other Additives]

The polymerizable composition may contain one type or two or more types of other additives such as an antioxidant, an ultraviolet absorbent, a sensitizing agent, a stabilizer, a plasticizer, a chain transfer agent, a polymerization inhibitor, an anti-foaming agent, a leveling agent, a thickener, a flame retardant, a surface-active substance, a dispersant, and a coloring material such as a dye and pigment.

<Film>

The polymerizable composition of the present invention is useful as a material of various optical films such as a phase difference film and a reflection film, and can form various optical films by using the polymerizable composition of the present invention.

[Manufacturing Method of Film]

An example of a manufacturing method of an optical film is a manufacturing method, including at least:

(i) applying a polymerizable composition onto a surface of a substrate or the like, and setting the polymerizable composition to be in a state of a liquid crystalline phase (a nematic liquid crystalline phase, a cholesteric liquid crystalline phase, or the like); and (ii) performing a curing reaction with respect to the polymerizable composition, and forming a cured film (liquid crystal layer) by immobilizing the liquid crystalline phase.

The steps of (i) and (ii) are repeated a plurality of times, and thus, it is possible to prepare a film in which a plurality of cured films described above are laminated. In addition, the plurality of cured films are bonded to each other by an adhesive, and thus, it is also possible to prepare the film in which the plurality of cured films are laminated.

In the step of (i), first, the polymerizable composition is applied onto the surface of the substrate or the surface of an alignment film formed on the substrate. It is preferable that the polymerizable composition is prepared as a coating liquid in which a material is dissolved and/or dispersed in a solvent. An organic solvent is preferably used as the solvent which is used for preparing the coating liquid. Examples of the organic solvent include amide (for example, N,N-dimethyl formamide); sulfoxide (for example, dimethyl sulfoxide); a heterocyclic compound (for example, pyridine); hydrocarbon (for example, benzene and hexane); alkyl halide (for example, chloroform and dichloromethane); ester (for example, methyl acetate, butyl acetate, and propylene glycol monoethyl ether acetate); ketone (for example, acetone, methyl ethyl ketone, cyclohexanone, and cyclopentanone); ether (for example, tetrahydrofuran, 1,2-dimethoxy ethane); 1,4-butane diol diacetate, and the like. Among them, the alkyl halide, the ester, and the ketone are particularly preferable. Two or more types of the organic solvents may be used together.

The coating liquid can be applied by various methods such as a wire bar coating method, an extrusion coating method, a direct gravure coating method, a reverse gravure coating method, and a die coating method. In addition, the composition is ejected from a nozzle of an ink jet device, and thus, the coated film can be formed.

Next, the polymerizable composition which is applied onto the surface and becomes the coated film is set to be in the state of the liquid crystalline phase such as a nematic liquid crystalline phase and a cholesteric liquid crystalline phase. In an aspect where the polymerizable composition is prepared as a coating liquid containing a solvent, there is a case where the coated film is dried, and the solvent is removed, and thus, it is possible to set the polymerizable composition to be in the state of the liquid crystalline phase. In addition, in order to set a transition temperature with respect to the liquid crystalline phase, as desired, the coated film may be heated. For example, first, the coated film is heated to a temperature of an isotropic phase, and then, is cooled to a liquid crystalline phase transition temperature, and the like, and thus, it is possible to stably set the polymerizable composition to be in the state of the liquid crystalline phase. The liquid crystalline phase transition temperature of the polymerizable composition is preferably in a range of 10° C. to 250° C., and is more preferably in a range of 10° C. to 150° C., from the viewpoint of manufacturing suitability or the like. In a case where the liquid crystalline phase transition temperature of the polymerizable composition is lower than 10° C., a cooling step or the like is required in order to decrease the temperature to a temperature range in which the liquid crystalline phase is exhibited. In addition, in a case where the liquid crystalline phase transition temperature of the polymerizable composition is higher than 250° C., first, a high temperature is required in order to set the polymerizable composition to be in an isotropic liquid state at a temperature higher than the temperature range in which the liquid crystalline phase is exhibited, and thus, this is disadvantageous from the viewpoint of the waste of thermal energy, the deformation of the substrate, deterioration, and the like.

Next, in the step of (ii), the coated film which is in the state of the liquid crystalline phase is cured. The curing may be performed by any polymerization method such as a radical polymerization method, an anionic polymerization method, a cationic polymerization method, and a coordination polymerization method. A suitable polymerization method may be selected according to the polymerizable compound represented by Formula (I). By this polymerization, it is possible to obtain a polymer having a unit derived from the polymerizable compound represented by Formula (I) in a constitutional unit.

In an example, a curing reaction is performed by ultraviolet ray irradiation. In the ultraviolet ray irradiation, a light source such as an ultraviolet ray lamp is used. In this step, the curing reaction of the composition is performed by the ultraviolet ray irradiation, and thus, the liquid crystalline phase (the nematic liquid crystalline phase, the cholesteric liquid crystalline phase, or the like) is immobilized, and the cured film (liquid crystal layer) is formed.

An irradiation energy amount of an ultraviolet ray is not particularly limited, but in general, is preferably approximately 0.1 J/cm$^2$ to 0.8 J/cm$^2$. In addition, a time for performing the ultraviolet ray irradiation with respect to the coated film is not particularly limited, and may be determined from the viewpoint of both of a sufficient hardness and sufficient productivity of the cured film.

In order to accelerate the curing reaction, the ultraviolet ray irradiation may be performed under heating conditions. In addition, it is preferable that a temperature at the time of performing the ultraviolet ray irradiation is maintained in a temperature range where the liquid crystalline phase is exhibited such that the liquid crystalline phase is not scattered. In addition, an oxygen concentration in the atmosphere is associated with a degree of polymerization, and thus, in a case where a desired degree of polymerization is not attained in the air, and the film hardness is insufficient, it is preferable to decrease the oxygen concentration in the atmosphere by a method such as nitrogen substitution.

In the step described above, the liquid crystalline phase is immobilized, and the cured film is formed. Here, a state where alignment of a compound formed of a liquid crystalline phase is retained is the most typical and preferred aspect as a state where the liquid crystalline phase is "immobilized". The state is not only limited to this, and specifically, indicates a state where a layer does not have fluidity, an alignment form is not changed by an external field or an external force, and an immobilized alignment form can be stably retained in a temperature range of generally 0° C. to 50° C., and in a temperature range of −30° C. to 70° C. in more rigorous conditions. In the present invention, it is preferable that the alignment state of the liquid crystalline phase is immobilized by the curing reaction which is performed by the ultraviolet ray irradiation.

The thickness of the cured film described above is not particularly limited. A preferred film thickness may be determined according to the application or according to optical properties to be desired. In general, the thickness is preferably 0.05 μm to 50 μm, and is more preferably 1.0 μm to 35 μm.

[Substrate]

The film may include a substrate. The material and the optical properties of the substrate are not particularly limited insofar as the substrate has self-supporting properties, and supports the cured film described above. The substrate can be selected from a glass plate, a quartz plate, a polymer film, and the like. According to the application, a substrate having high transparency with respect to ultraviolet light may be used. Examples of a polymer film having high transmittance with respect to visible light include polymer films for various optical films which are used as a member of a display device such as a liquid crystal display device. Examples of the substrate include a polyester film such as polyethylene terephthalate (PET), polybutylene terephthalate, and polyethylene naphthalate (PEN); a polycarbonate (PC) film, a polymethyl methacrylate film; a polyolefin film such as polyethylene and polypropylene; a polyimide film, a triacetyl cellulose (TAC) film, and the like. The polyethylene terephthalate film and the triacetyl cellulose film are preferable.

[Alignment Layer]

The film may include an alignment layer between the substrate and the cured film. The alignment layer has a function of more accurately defining an alignment direction of the liquid crystal compound. The alignment layer can be disposed by means such as a rubbing treatment of an organic compound (preferably, a polymer), oblique vapor deposition of an inorganic compound, and formation of a layer having a microgroove. Further, an alignment layer is also known in which an alignment function is generated by applying an electric field, by applying a magnetic field, or by performing light irradiation. It is preferable that the alignment layer is formed by performing a rubbing treatment with respect to a surface of a polymer film.

A polymer of an organic compound is preferable as a material to be used in the alignment layer, a polymer which can be cross-linked by itself or a polymer which is cross-linked by a cross-linking agent is commonly used. It is natural that a polymer having both functions is also used. Examples of the polymer can include a polymer such as polymethyl methacrylate, an acrylic acid/methacrylic acid copolymer, a styrene/malein imide copolymer, polyvinyl alcohol and modified polyvinyl alcohol, poly(N-methylol acryl amide), a styrene/vinyl toluene copolymer, chlorosulfonated polyethylene, nitrocellulose, polyvinyl chloride, chlorinated polyolefin, polyester, polyimide, a vinyl acetate/vinyl chloride copolymer, an ethylene/vinyl acetate copolymer, carboxy methyl cellulose, gelatine, polyethylene, polypropylene, and polycarbonate, and a compound such as a silane coupling agent. Preferred examples of the polymer include a water-soluble polymer such as poly(N-methylol acryl amide), carboxy methyl cellulose, gelatine, and polyvinyl alcohol and modified polyvinyl alcohol, and among them, the gelatine, and the polyvinyl alcohol and the modified polyvinyl alcohol are preferable, and in particular, the polyvinyl alcohol and the modified polyvinyl alcohol are preferable.

[Adhesive Layer]

In a case where a plurality of cured films are bonded to each other by an adhesive, an adhesive layer is disposed between the cured films. The adhesive layer may be formed of an adhesive.

Examples of the adhesive include a hot melt type adhesive, a thermal curing type adhesive, a photocuring type adhesive, a reaction curing type adhesive, and a pressure sensitive adhesive type adhesive which is not necessary to be cured, from the viewpoint of a curing method, and a compound such as an acrylate-based compound, a urethane-based compound, a urethane acrylate-based compound, an epoxy-based compound, an epoxy acrylate-based compound, a polyolefin-based compound, a modified olefin-based compound, a polypropylene-based compound, an ethylene vinyl alcohol-based compound, a vinyl chloride-based compound, a chloroprene rubber-based compound, a cyanoacrylate-based compound, a polyamide-based compound, a polyimide-based compound, a polystyrene-based compound, and a polyvinyl butyral-based compound can be used as the material of each of the adhesives. The photocuring type adhesive is preferable as the curing method from the viewpoint of workability and productivity, and the acrylate-based compound, the urethane acrylate-based compound, the epoxy acrylate-based compound, and the like are preferably used as the material of the adhesive from the viewpoint of optical transparency and heat resistance.

The film thickness of the adhesive layer is 0.5 μm to 10 μm, and is preferably 1.0 μm to 5.0 μm. In a case where the adhesive layer is used as a half mirror for displaying a projection image, it is preferable that the adhesive layer is disposed with an even film thickness in order to reduce color unevenness or the like.

[Application of Film]

An Example of the film formed by using the polymerizable composition includes a film formed by immobilizing alignment (for example, horizontal alignment, vertical alignment, hybrid alignment, and the like) of a liquid crystalline phase of a polymerizable composition. In general, such a film has optical anisotropy, and is used as an optical compensation film or the like of a liquid crystal display device or the like.

Another example of the film includes a film which includes a layer formed by immobilizing a cholesteric liquid crystalline phase of a polymerizable composition and has selective reflection properties with respect to light in a predetermined wavelength range.

In the cholesteric liquid crystalline phase, liquid crystal molecules are arranged into the shape of a spiral. The layer formed by immobilizing the cholesteric liquid crystalline phase (hereinafter, may be referred to as a "cholesteric liquid crystal layer") functions as a circularly polarized light selective reflection layer which selectively reflects any one of right circularly polarized light and left circularly polarized light in a selective reflection wavelength range, and transmits the other sense of circularly polarized light. A film including one or two or more cholesteric liquid crystal layers can be used in various applications. In a film including two or more cholesteric liquid crystal layers, the senses of circularly polarized light rays which are reflected on the respective cholesteric liquid crystal layers may be identical to each other or opposite to each other according to the application. In addition, the center wavelengths of the selective reflections of the respective cholesteric liquid crystal layers described below may also be identical to each other or different from each other according to the application.

Furthermore, herein, the "sense" of the circularly polarized light indicates whether the circularly polarized light is right circularly polarized light or left circularly polarized light. In the sense of the circularly polarized light, in a case of observing light such that the light propagates towards the front side thereof, a case where a distal end of an electric field vector is rotated in a clockwise direction according to an increase in time is defined as right circularly polarized light, and a case where the distal end of the electric field vector is rotated in a counterclockwise direction is defined as left circularly polarized light. Herein, the term of "sense" may be used in a twisted direction of a spiral of a cholesteric liquid crystal. In the selective reflection of the cholesteric liquid crystal, in a case where the twisted direction (the sense) of the spiral of the cholesteric liquid crystal is in a right direction, the right circularly polarized light is reflected, and the left circularly polarized light is transmitted, and in a case where the sense is in a left direction, the left circularly polarized light is reflected, and the right circularly polarized light is transmitted.

For example, a film including a cholesteric liquid crystal layer having selective reflection properties in a visible light wavelength range (a wavelength of 400 nm to 750 nm) can be used as a screen or a half mirror for displaying a projection image. In addition, the film can be used as a color filter or a filter which improves a color purity of display light of a display (for example, refer to JP2003-294948A) by controlling a reflection range.

In addition, the optical film can be used in various applications such as a polarization element, a reflection film, an antireflection film, a view angle compensation film, a holography, and an alignment film, which are constituents of an optical element.

Hereinafter, an application as a member for displaying a projection image, which is a particularly preferred application, will be described.

[Member for Displaying Projection Image]

At a wavelength where projection light is selectively reflected by the function of the cholesteric liquid crystal layer described above, any one sense of the circularly polarized light is reflected, and thus, a projection image can be formed. The projection image may be an image which is displayed on the surface of the member for displaying a projection image and is viewed in this way, or may be a virtual image that emerges from the front of the member for displaying a projection image in a case of being observed by an observer.

A center wavelength $\lambda$ of the selective reflection described above depends on a pitch P (=a cycle of a spiral) of a spiral structure in a cholesteric liquid crystalline phase, and corresponds to a relationship of $\lambda = n \times P$ with an average refractive index n of the cholesteric liquid crystal layer. Furthermore, here, the center wavelength $\lambda$ of the selective reflection of the cholesteric liquid crystal layer indicates a wavelength in a centroid position of a reflection peak of a circularly polarized light reflection spectrum measured from a normal direction of the cholesteric liquid crystal layer. As apparent from the expression described above, the pitch of the spiral structure is adjusted, and thus, the center wavelength of the selective reflection can be adjusted. That is, an n value and a P value are adjusted, and for example, the center wavelength $\lambda$ is adjusted in order to selectively reflect any one of right circularly polarized light and left circularly polarized light with respect to blue light, and thus, it is possible to set the center wavelength of the selective reflection on appearance to be in a wavelength range of 450 nm to 495 nm. Furthermore, the center wavelength of the selective reflection on appearance indicates the wavelength in the centroid position of the reflection peak of the circularly polarized light reflection spectrum of the cholesteric liquid crystal layer measured from an observation direction at the time of being practically used (at the time of being used as the member for displaying a projection image). The pitch of the cholesteric liquid crystalline phase depends on the type of chiral agent which is used along with the polymerizable liquid crystal compound, or the addition concentration thereof, and thus, a desired pitch can be obtained by adjusting the type of chiral agent or the addition concentration thereof. Furthermore, methods described in "Introduction of Liquid Crystal Chemical Experiments" of The Japanese Liquid Crystal Society, published by Sigma Publishing Company in 2007, p. 46, and "Liquid Crystal Handbook" of Editorial Committee of Liquid Crystal Handbook, published by MARUZEN-YUSHODO Company, Limited, p. 196 can be used as a measurement method of the sense of the spiral or the pitch.

A half-width $\Delta\lambda$ (nm) of the selective reflection wavelength range where circularly polarized light selective reflection is exhibited depends on birefringence $\Delta n$ of the liquid crystal compound and the pitch P described above, and corresponds to a relationship of $\Delta\lambda = \Delta n \times P$. For this reason, the width of the selective reflection wavelength range can be controlled by adjusting $\Delta n$. That is, in the cholesteric liquid crystal layer formed of the composition containing the polymerizable liquid crystal compound having low birefringence of the present invention, it is possible to increase the wavelength selectivity of the selective reflection.

For example, $\Delta\lambda/\lambda$, which is a ratio of the half-width $\Delta\lambda$ of the selective reflection wavelength range to the center wavelength $\lambda$ of the selective reflection, can be used as an index indicating the wavelength selectivity of the selective reflection. In the film of the present invention, in particular, in the film which is used as the member for displaying a projection image, $\Delta\lambda/\lambda$ is preferably less than or equal to 0.09, and is more preferably less than or equal to 0.07. More specifically, in the cholesteric liquid crystal layer of the film, it is preferable that $\Delta\lambda/\lambda$ satisfies the range described above, and in each of the two or more cholesteric liquid crystal layers of the film including the two or more cholesteric liquid crystal layers, it is preferable that $\Delta\lambda/\lambda$ satisfies the range described above. Furthermore, $\Delta\lambda$'s and $\lambda$'s of the respective layers may be respectively identical to each other or different from each other.

Each cured film having a center wavelength of selective reflection on appearance in each of a red light wavelength range, a green light wavelength range, and a blue light wavelength range is prepared by using the polymerizable composition described above, and the cured films are laminated, and thus, a member for displaying a projection image which can display a full color projection image can be prepared. Specifically, in a half mirror, it is preferable that cured films having different center wavelengths of selective reflections (for example, different by greater than or equal to 50 nm) in each of ranges of 750 nm to 620 nm, 630 nm to 500 nm, and 530 nm to 420 nm are laminated.

The center wavelength of the selective reflection of each of the cured films is adjusted according to a light emission wavelength range of a light source to be used in projection and a use aspect of the member for displaying a projection image, and thus, a clear projection image with excellent light utilization efficiency can be displayed. In particular, each of the center wavelengths of the selective reflections of the cured films is adjusted according to the light emission wavelength range of the light source to be used in the projection, and the like, and thus, a clear color projection image with excellent light utilization efficiency can be displayed. In particular, the use aspect of the member for displaying a projection image includes an incidence angle of projection light on the surface of the half mirror for displaying a projection image, a projection image observation direction on the surface of the member for displaying a projection image, and the like.

For example, the member for displaying a projection image described above is configured to have transmittance with respect to light in a visible light range, and thus, can be used as a half mirror which can be used as a combiner of a head-up display. The half mirror for displaying a projection image can visibly display an image projected from a projector or the like, and simultaneously, when the half mirror for displaying a projection image is observed from the same surface side as the surface on which the image is displayed, information and scenery on the opposite surface side can be observed.

When the member for displaying a projection image is used as a half mirror for displaying a projection image, it is preferable that the cured film prepared as described above, in particular, a laminate of three or more cured films is disposed on a surface of a base material. It is preferable that the base material is transparent and has low birefringence in a visible light range. For example, a phase difference of the base material at a wavelength of 550 nm is preferably less than or equal to 50 nm, and is more preferably less than or equal to 20 nm.

Examples of the base material include inorganic glass or a polymer resin (an acrylic resin (acrylic acid esters such as polymethyl (meth)acrylate, and the like), cyclic polyolefin such as polycarbonate, cyclopentadiene-based polyolefin, or norbornene-based polyolefin, polyolefins such as polypropylene, aromatic vinyl polymers such as polystyrene, polyarylate, cellulose acylate, and the like). Among them, from the viewpoint of low birefringence, inorganic glass, an acrylic resin, cyclic polyolefin, polyolefins, or cellulose acylate is preferable, and inorganic glass or an acrylic resin is more preferable.

The half mirror for displaying a projection image may include an antireflection layer. It is preferable that the antireflection layer is provided on the outermost surface. The antireflection layer may be disposed on the outermost surface which becomes a viewing side at the time of using the half mirror for displaying a projection image, or may be disposed on the outermost surface on the opposite side, and it is preferable that the antireflection layer is disposed on the outermost surface on the viewing side. In a case where the cured film is disposed on the surface of the base material, the antireflection layer may be disposed on both of the surface on the base material side and the surface on the cured film side which becomes the viewing side. According to such a configuration, a double image, which is particularly generated in a case where the birefringence of the base material is high, is rarely generated.

Examples of the antireflection layer include a film having a configuration of a two-layer film in which a layer of high refractive index and a layer of low refractive index are combined, a film having a configuration of three-layer film in which a layer of intermediate refractive index, a layer of high refractive index, and a layer of low refractive index are sequentially laminated, and the like, in addition to a film in which fine surface concavities and convexities are formed.

Configuration examples include a configuration including two layers of a layer of high refractive index/a layer of low refractive index in this order from a lower side, a configuration including three layers having different refractive indices, in which a layer of intermediate refractive index (a layer having a refractive index which is higher than that of a underlayer and is lower than that of a layer of high refractive index)/a layer of high refractive index/a layer of low refractive index are laminated in this order, and the like, and it is also proposed that more antireflection layers are laminated. Among them, it is preferable that a layer of intermediate refractive index/a layer of high refractive index/a layer of low refractive index are provided on a hard coat layer in this order, from the viewpoint of durability, optical properties, costs, productivity, and the like, and examples of the configuration include configurations described in JP1996-122504A (JP-H08-122504A), JP1996-110401A (JP-H08-110401A), JP1998-300902A (JP-H10-300902A), JP2002-243906A, JP2000-111706A, and the like. In addition, an antireflection film having a three-layer configuration, which has excellent robustness with respect to a variation in a film thickness, is described in JP2008-262187A. In a case where the antireflection film having a three-layer configuration described above is disposed on a surface of an image display device, it is possible to set an average value of reflectivity to be less than or equal to 0.5%, to considerably reduce reflected glare, and to obtain an image having excellent stereoscopic effects. In addition, other functions may be imparted to each layer, and examples of a layer to which other functions are imparted include a layer of low refractive index having antifouling properties, a layer of high refractive index having antistatic properties, a hard coat layer having antistatic properties, and a hard coat layer having anti-glare characteristics (for example, JP1998-206603A (JP-H10-206603A), JP2002-243906A, JP2007-264113A, and the like), and the like.

Examples of an inorganic material configuring the antireflection layer include $SiO_2$, $SiO$, $ZrO_2$, $TiO_2$, $TiO$, $Ti_2O_3$, Ti$_2$O$_5$, Al$_2$O$_3$, Ta$_2$O$_5$, CeO$_2$, MgO, Y$_2$O$_3$, SnO$_2$, MgF$_2$, WO$_3$, and the like, and one type of material can be independently used, or two or more types thereof can be used together. Among them, SiO$_2$, ZrO$_2$, TiO$_2$, and Ta$_2$O$_5$ are preferable since vacuum vapor deposition can be performed at a low temperature, and thus, a film can also be formed on a surface of a plastic substrate.

A laminated structure of alternately forming a layer of high refractive index and a layer of low refractive index, in which the total optical film thickness of a ZrO$_2$ layer and a SiO$_2$ layer from the substrate side is λ/4, an optical film thickness of the ZrO$_2$ layer is λ/4, and an optical film thickness of the SiO$_2$ layer which is the outermost layer is λ/4, is exemplified as a multilayer film which is formed of the inorganic material. Here, λ is a design wavelength, and a wavelength of 520 nm is generally used. It is preferable that the outermost layer is formed of SiO$_2$ since a refractive index is low, and a mechanical hardness can be imparted to the antireflection layer.

In a case where the antireflection layer is formed of the inorganic material, for example, a vacuum vapor deposition method, an ion plating method, a sputtering method, a CVD method, a method of performing precipitation in a saturated solution by a chemical reaction, and the like can be adopted as a film formation method.

Examples of an organic material which is used in the layer of low refractive index can include a tetrafluoroethylene-hexafluoropropylene copolymer (FFP), polytetrafluoroethylene (PTFE), an ethylene-tetrafluoroethylene copolymer (ETFE), and the like, and a composition containing a fluorine-containing curable resin and inorganic fine particles, which is described in JP2007-298974A, a low refractive index coating composition containing hollow silica fine particles, which is described in JP2002-317152A, JP2003-202406A, and JP2003-292831A can be suitably used. The film formation method can be performed by coating methods such as a spin coating method, a dip coating method, and a gravure coating method, which have excellent productivity, in addition to the vacuum vapor deposition method.

The refractive index of the layer of low refractive index is preferably 1.30 to 1.51. The refractive index of the layer of low refractive index is more preferably 1.30 to 1.46, and is even more preferably 1.32 to 1.38.

Examples of an organic material which is used in the layer of intermediate refractive index and the layer of high refractive index can include a binder which is obtained by crosslinking or a polymerization reaction, such as an ionizing radiation curable compound having an aromatic ring, an ionizing radiation curable compound containing a halogenated element other than fluorine (for example, Br, I, Cl, and the like), and an ionizing radiation curable compound containing an atom such as S, N, and P, and inorganic particles containing TiO$_2$ to be added to the binder as a main component. Specifically, an organic material described in paragraphs [0074] to [0094] of JP2008-262187A can be exemplified.

The refractive index of the layer of high refractive index is preferably 1.65 to 2.20, and is more preferably 1.70 to 1.80. The refractive index of the layer of intermediate refractive index is adjusted to be a value between the refractive index of the layer of low refractive index and the refractive index of the layer of high refractive index. The refractive index of the layer of intermediate refractive index is preferably 1.55 to 1.65, and is more preferably 1.58 to 1.63.

The film thickness of the antireflection layer is not particularly limited, but may be approximately 0.1 μm to 10 μm, 1.0 μm to 5.0 μm, and 2.0 μm to 4.0 μm.

EXAMPLES

Hereinafter, the characteristics of the present invention will be described in detail with reference to the examples and comparative examples. Materials, use amounts, ratios, treatment contents, treatment sequences, and the like of the following examples can be suitably changed unless the changes cause deviance from the gist of the present invention. Accordingly, the range of the present invention will not be restrictively interpreted by the following specific examples.

In the examples, LC-MS indicates liquid chromatography-mass spectrometry, HPLC indicates high performance liquid chromatography, and NMR indicates nuclear magnetic resonance.

Synthesis Example

[Synthesis of Compound 1-3]

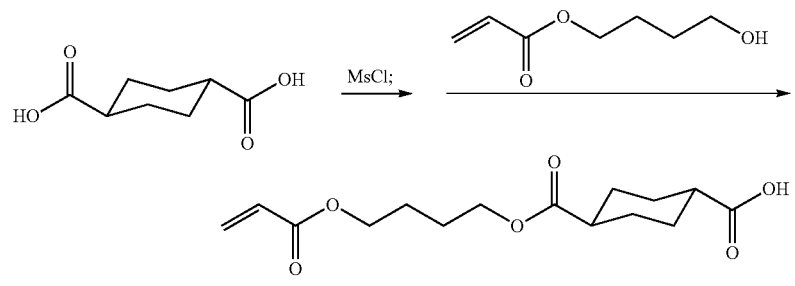

Carboxylic Acid I-9

A trans-1,4-cyclohexane dicarboxylic acid (10 g), mesyl chloride (1.9 mL), and BHT (0.2 g) were stirred in THF (72 mL), and triethyl amine (3.7 mL) was subjected to dropwise addition by retaining an internal temperature to be lower than or equal to 25° C. Stirring was performed at a room temperature for 2 hours, and then, N,N-dimethyl aminopyridine (0.3 g) and 4-hydroxy butyl acrylate (3.1 g) were added, and triethyl amine (3.7 mL) was subjected to dropwise addition at an internal temperature of lower than or equal to 25° C. Stirring was performed at a room temperature for 3 hours, and then, a water layer was removed by adding dilute hydrochloric acid and ethyl acetate and washing was sequentially performed with dilute hydrochloric acid, saturated sodium bicarbonate water, and saline. An organic layer was dried with magnesium sulfate, the desiccant was filtered, and then, a solvent was distilled under reduced pressure, and thus, a carboxylic acid I-9 (7.1 g) was obtained.

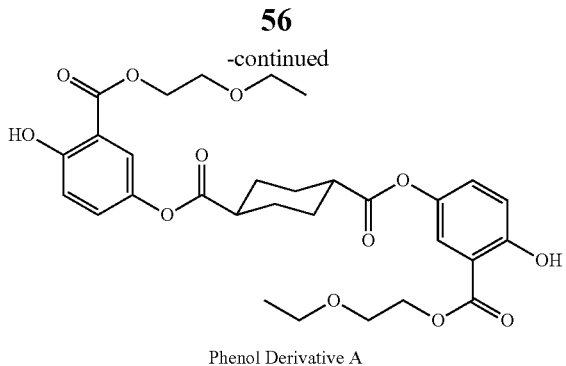

Phenol Derivative A

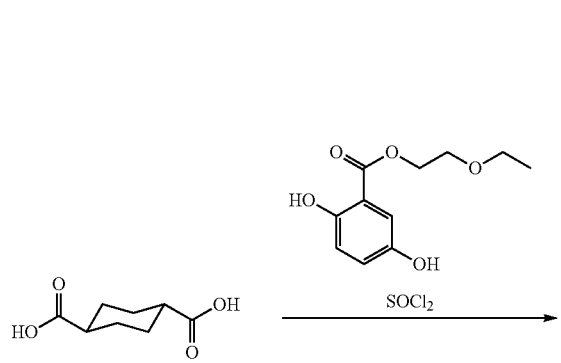

A mixture of a trans-1,4-cyclohexane dicarboxylic acid (5 g), toluene (40 mL), and N,N-dimethyl formamide (0.05 mL) was heated and stirred, thionyl chloride (8.3 g) was subjected to dropwise addition at an internal temperature of 80° C., and then, heating and stirring were performed at an internal temperature 80° C. for 2 hours. Cooling was performed to an internal temperature of 30° C., and then, 2-ethoxy ethyl-2,5-dihydroxy benzoate (13.1 g) was added, and then, heating and stirring were performed at an internal temperature of 90° C. for 4 hours. Methanol (60 mL) was added at an internal temperature of 40° C., and then, stirring was further performed at an internal temperature 5° C. for 30 minutes, and generated crystals were filtered, and thus, 11.5 g of a phenol derivative A was obtained.

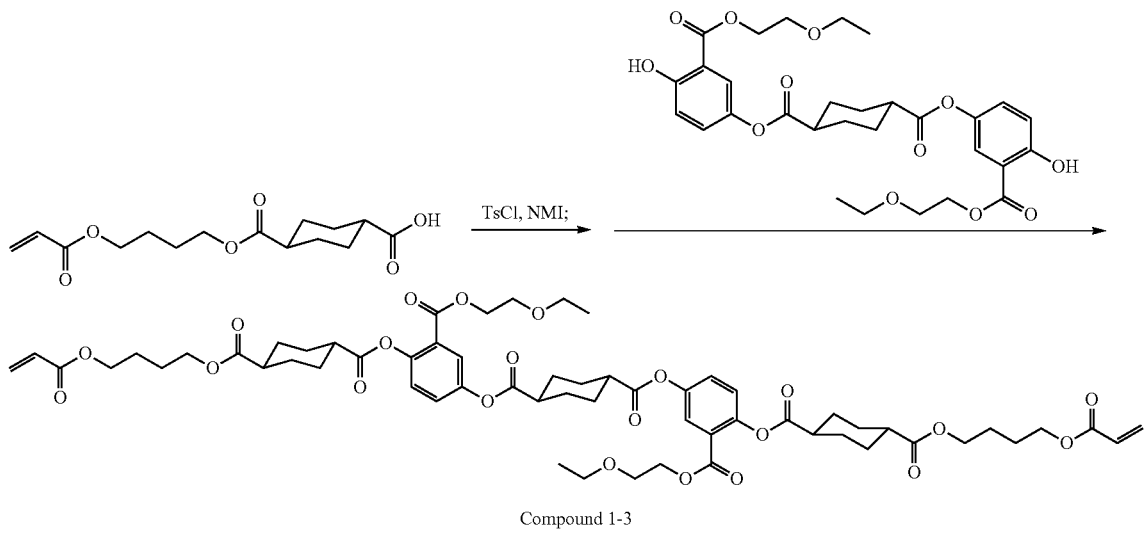

Compound 1-3

The carboxylic acid I-9 (13.4 g), TsCl (10.3 g), and BHT (0.2 g) were stirred in THF (40 mL) and 1-ethyl-2-pyrrolidone (25 mL), 1-methyl imidazole (11 mL) was subjected to dropwise addition under ice cooling, and stirring was performed at a room temperature for 1 hour. The phenol derivative A (10.6 g) was added, and stirring was further performed at a room temperature for 2 hours. Water (10 mL) was added, and then, a water layer was removed, water and methanol were added, stirring was performed for 1 hour under ice cooling, and generated crystals were filtered, and thus, a compound 1-3 (18.3 g) was obtained.

$^1$H-NMR (Solvent: CDCl$_3$) δ(ppm):

1.2 (t, 6H), 1.4-1.8 (m, 18H), 2.1-2.2 (m, 4H), 2.2-2.4 (m, 12H), 2.5-2.7 (m, 4H), 3.5 (q, 4H), 3.7-3.8 (m, 4H), 4.1-4.3 (m, 8H), 4.4-4.5 (m, 4H), 5.8 (dd, 2H), 6.1 (dd, 2H), 6.4 (dd, 2H), 7.1 (d, 2H), 7.3 (dd, 2H), 7.7 (d, 2H)

[Synthesis of Composition (MI-1) of Compounds 1-3 and 1-34]

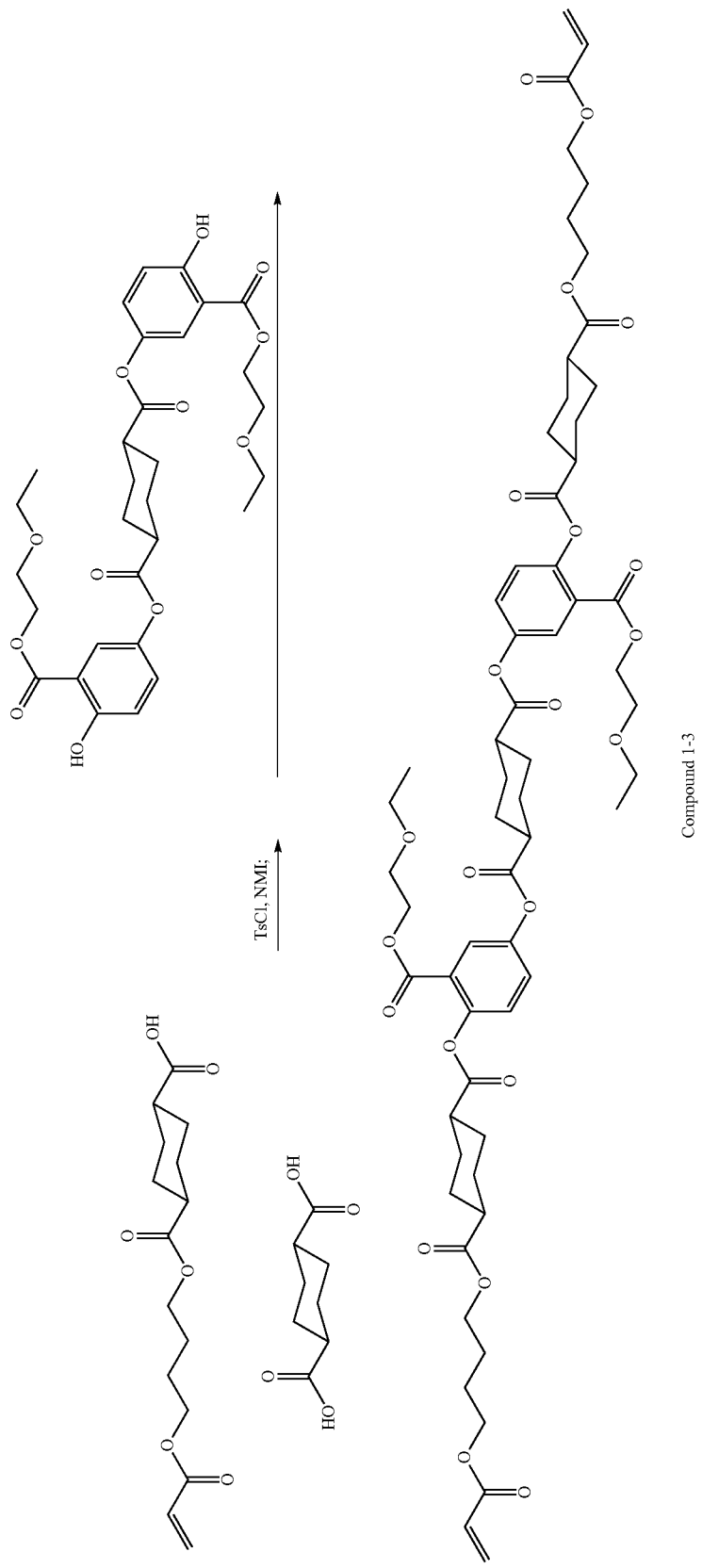
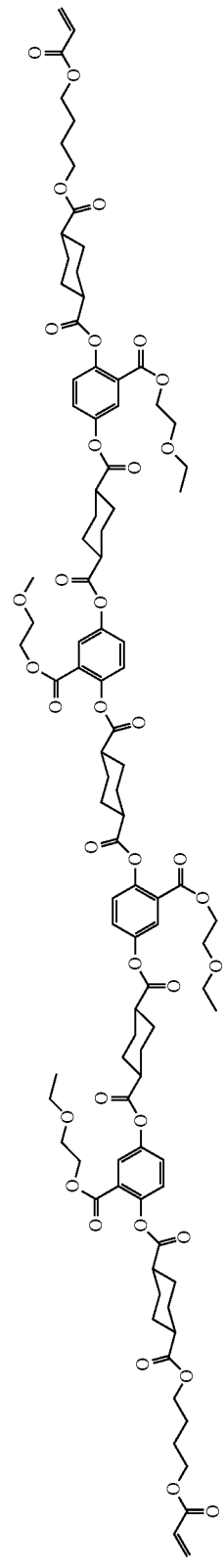
Compound 1-3
Compound 1-34

The carboxylic acid I-9 (7.9 g), trans-1,4-cyclohexane dicarboxylic acid (0.6 g), TsCl (6.5 g), and BHT (0.2 g) were stirred in THF (20 mL) and 1-ethyl-2-pyrrolidone (13 mL), 1-methyl imidazole (6.8 mL) was subjected to dropwise addition under ice cooling, and stirring was performed at a room temperature for 1 hour. The phenol derivative A (5.0 g) was added, and stirring was further performed at a room temperature for 2 hours. Water (5 mL), ethyl acetate (20 mL), and acetone (5 mL) were added, and then were stirred for 10 minutes, a water layer was removed, water and methanol were added, stirring was performed for 1 hour under ice cooling, and generated solids were filtered to obtain a crude product. Next, the crude product was subjected to recrystallization by using THF, ethyl acetate, water, and methanol, and thus, a mixture (5.8 g) of the compound 1-3 and a compound 1-34 was obtained.

LC-MS measurement (positive (cation) observation):

| | |
|---|---|
| Compound 1-3 | 1146 (detected by M + NH$_4$) |
| Compound 1-34 | 1891 (detected by M + H$_3$O) |

HPLC Measurement:

The obtained composition was analyzed in acetonitrile/water-based HPLC (column: TSKgel ODS-100Z, manufactured by TOSOH CORPORATION, detection wavelength: 254 nm), and as a result, a ratio of a peak surface area corresponding to the compound 1-3 was 82% and a ratio of a peak surface area corresponding to the compound 1-34 was 16%.

$^1$H-NMR (Solvent: CDCl$_3$) δ(ppm):
1.2 (t), 1.4-1.8 (m), 2.1-2.2 (m), 2.2-2.4 (m), 2.5-2.7 (m), 3.5-3.6 (m), 3.7-3.8 (m), 4.1-4.3 (m), 4.35-4.45 (m), 5.8 (dd), 6.1 (dd), 6.4 (dd), 7.0-7.1 (m), 7.25-7.3 (m), 7.7 (d)

A mass ratio of the compound 1-3 to the compound 1-34 in a composition (MI-1) calculated from a proton ratio was 78:22.

[Synthesis of Compound 1-20]

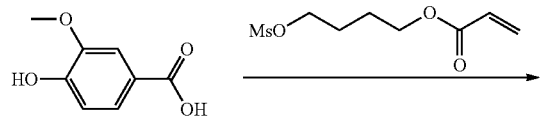

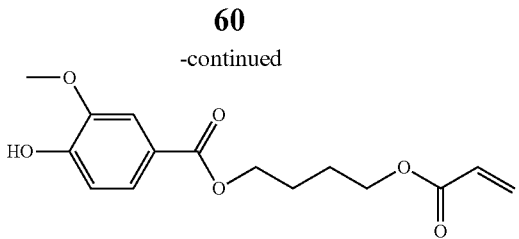

Phenol Derivative B

A vanillic acid (10.9 g) was stirred in dimethyl acetoamide (70 mL), triethyl amine (9.8 mL), methane sulfonic acid 4-acryloyloxy butyl (11.1 g), and BHT (0.2 g) were added, and stirring was performed at an internal temperature of 70° C. for 10 hours. Cooling was performed to 30° C., and then, a water layer was removed by adding water and ethyl acetate, and washing was sequentially performed with saturated sodium bicarbonate water, a dilute hydrochloric acid, and saline. An organic layer was dried with magnesium sulfate, the desiccant was filtered, and then, a solvent was distilled under reduced pressure by adding BHT (0.1 g), and thus, a phenol derivative B was obtained.

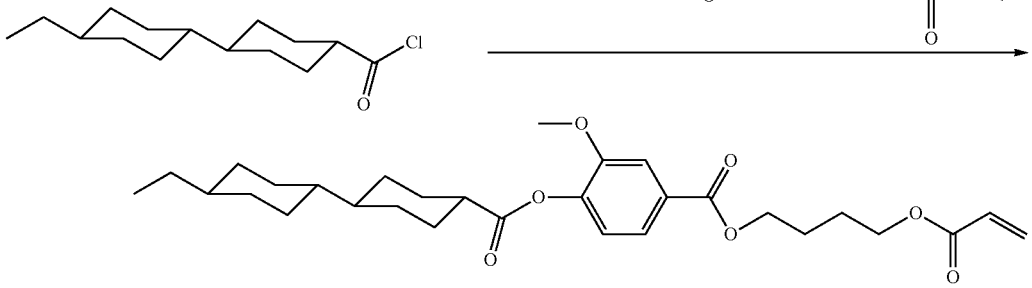

Compound 1-20

The phenol derivative B (13.1 g) was stirred in tetrahydrofuran (70 mL), and dimethyl aminopyridine (0.3 g) and acid chloride (12.7 g) of trans-4-ethylcyclohexyl-trans-4-cyclohexylcarboxylic acid were added. A reaction liquid was cooled to an internal temperature of 0° C., triethyl amine (7.6 mL) was subjected to dropwise addition, stirring was performed at 25° C. for 2 hours, and stirring was further performed for 30 minutes by adding methanol (20 mL). A water layer was removed by adding water and ethyl acetate, washing was sequentially performed with saturated sodium bicarbonate water, a dilute hydrochloric acid, and saline, and then, an organic layer was dried with magnesium sulfate, and the desiccant was filtered. A solvent was distilled under reduced pressure by adding BHT (0.1 g), cooling was performed to an internal temperature of 0° C. by adding methanol (80 mL), and crystals which were generated by performing stirring for 3 hours were filtered, and thus, 13 g of a compound 1-20 was obtained.

$^1$H-NMR (Solvent: CDCl$_3$) δ(ppm):
0.8-1.3 (m, 14H), 1.5-1.6 (m, 2H), 1.7-1.9 (m, 10H), 2.1-2.2 (m, 2H), 2.5-2.6 (m, 1H), 3.9 (s, 3H), 4.2 (t, 2H), 4.4 (t, 2H), 5.8 (dd, 1H), 6.1 (dd, 1H), 6.4 (dd, 1H), 7.0 (d, 1H), 7.6-7.7 (m, 2H)

[Synthesis of Compound 70]

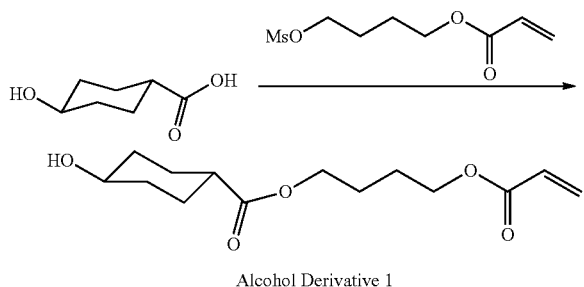

Alcohol Derivative 1

A trans-4-hydroxycyclohexane carboxylic acid (3.2 g) was stirred in dimethylacetamide (10 mL), triethyl amine (3.3 mL), a methane sulfonic acid 4-acryloyloxy butyl (4.4 g), and BHT (0.1 g) were added, and stirring was performed at an internal temperature of 70° C. for 6 hours. Cooling was performed to a temperature of 30° C., a water layer was removed by adding water and ethyl acetate, and washing was sequentially performed with saturated sodium bicarbonate water, a dilute hydrochloric acid, and saline. An organic layer was dried with magnesium sulfate, the desiccant was filtered, and then, a solvent was distilled under reduced pressure by adding BHT (0.1 g), and thus, an alcohol derivative 1 was obtained.

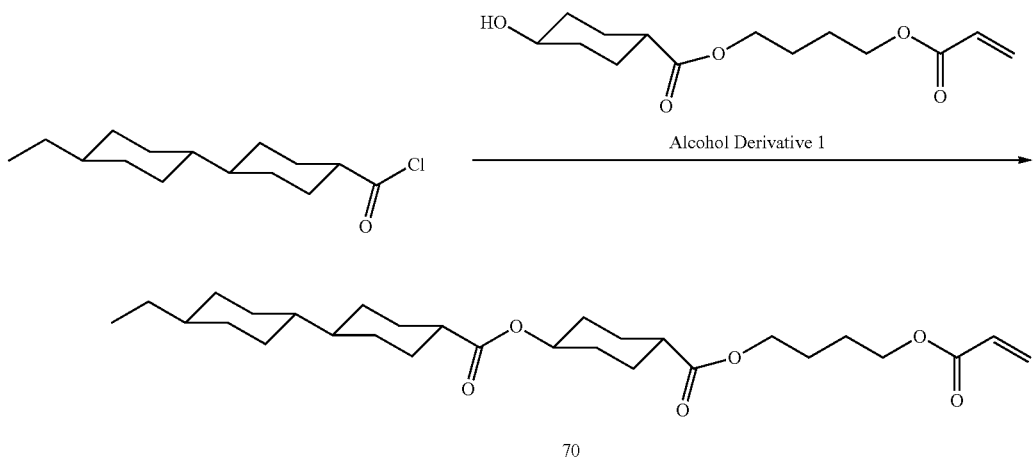

70

The alcohol derivative 1 (3.4 g) was stirred in 18 mL of tetrahydrofuran, and dimethyl aminopyridine (0.1 g) and acid chloride (3.7 g) of trans-4-ethylcyclohexyl-trans-4-cyclohexylcarboxylic acid were added. A reaction liquid was cooled to an internal temperature of 0° C., triethyl amine (2.3 mL) was subjected to dropwise addition, stirring was performed at 25° C. for 5 hours, and stirring was further performed for 30 minutes by adding methanol (30 mL) and water (15 mL). Crystals which were generated by performing cooling to an internal temperature of 0° C. were filtered, and were subjected to recrystallization by using ethyl acetate (10 mL) and methanol (20 mL), the generated crystals were filtered, and thus, 2.5 g of a compound 70 was obtained.

$^1$H-NMR (Solvent: CDCl$_3$) δ(ppm):
0.7-1.1 (m, 12H), 1.1-1.2 (m, 2H), 1.3-1.4 (m, 4H), 1.5-1.6 (m, 2H), 1.6-1.8 (m, 10H), 1.9-2.1 (m, 6H), 2.1-2.2 (m, 1H), 2.2-2.3 (m, 1H), 4.1 (t, 2H), 4.2 (t, 2H), 4.6-4.7 (m, 1H), 5.8 (dd, 1H), 6.1 (dd, 1H), 6.4 (dd, 1H)

[Synthesis of Compound 56]

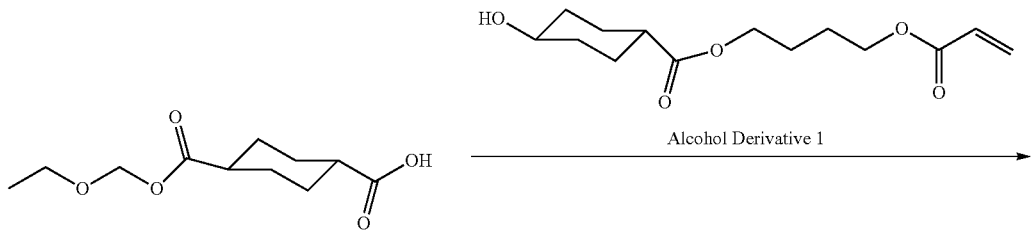

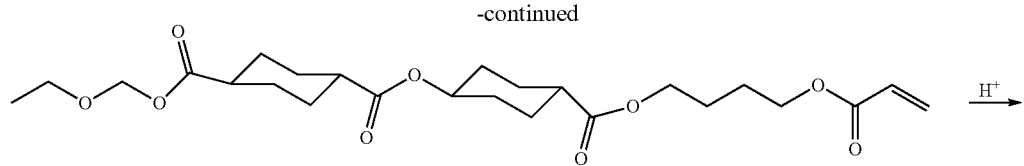

Ester Derivative 1

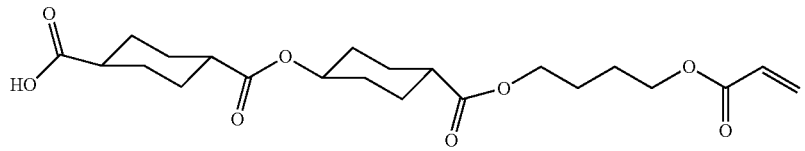

Carboxylic Acid Derivative 1

Trans-1,4-cyclohexane dicarboxylic acid monoethoxymethyl ester (1.5 g) was stirred in dimethylacetamide (7 mL), alcohol derivative (2.0 g), BHT (0.1 g), and dimethyl aminopyridine (0.08 g) were added, and Cooling was performed to a temperature of 0° C. 1-(3-Dimethylaminopropyl)-3-ethylcarbodiimide hydrochloride (WSCD HCl) (1.5 g) was added little by little, and stirring was performed for 3 hours. A 1 M dilute hydrochloric acid was added thereto, stirring was further performed for 5 minutes, then a water layer was removed by adding ethyl acetate, and washing was sequentially performed with a dilute hydrochloric acid, saturated sodium bicarbonate water, and saline. An organic layer was dried with magnesium sulfate, the desiccant was filtered, and then, a solvent was distilled under reduced pressure by adding BHT (0.1 g).

Next, 7 mL of tetrahydrofuran, 0.12 mL of water, and 0.12 g of p-toluenesulfonic acid monohydrate were added to an ester derivative 1 which is a reactive composition, and stirring was performed at a temperature 50° C. for 2 hours. A solvent was distilled under reduced pressure, n-hexane was added thereto, generated crystals were filtered and were dissolved in ethyl acetate, purification of a silica gel column chromatography was performed, and thus, a carboxylic acid derivative 1 was obtained.

A solution obtained by mixing the carboxylic acid derivative 1 (1.0 g) with ethyl acetate (3 mL) and diisopropylethylamine (0.45 mL) was gradually added dropwise to a solution of methanesulfonyl chloride (0.2 mL) in tetrahydrofuran (4 mL) under ice cooling. Stirring was performed for 1 hour under ice cooling, dimethyl aminopyridine (0.03 g) and a solution of methyl gentisate (0.16 g) in tetrahydrofuran (4 mL) were added dropwise, and then, triethyl amine (0.35 mL) was gradually added dropwise under ice cooling. A reaction temperature was set to 20° C., stirring was performed for 3 hours, then methanol was added thereto, a water layer was removed by further adding water and ethyl acetate, and washing was sequentially performed with a saturated sodium bicarbonate water, dilute hydrochloric acid, and saline. An organic layer was dried with magnesium sulfate, the desiccant was filtered, a solvent was distilled under reduced pressure by adding BHT (0.1 g), purification of a silica gel column chromatography was performed, and thus, 0.7 g of a compound 56 was obtained.

$^1$H-NMR (Solvent: CDCl$_3$) δ(ppm):
1.35-1.8 (m, 30H), 2.0-2.4 (m, 18H), 2.5-2.7 (m, 2H), 3.85 (s, 3H), 4.1-4.25 (m, 8H), 4.7-4.8 (m, 2H), 5.8 (dd, 2H), 6.15 (dd, 2H), 6.4 (dd, 2H), 7.1 (dd, 1H), 7.3 (dd, 1H), 7.8 (d, 1H)

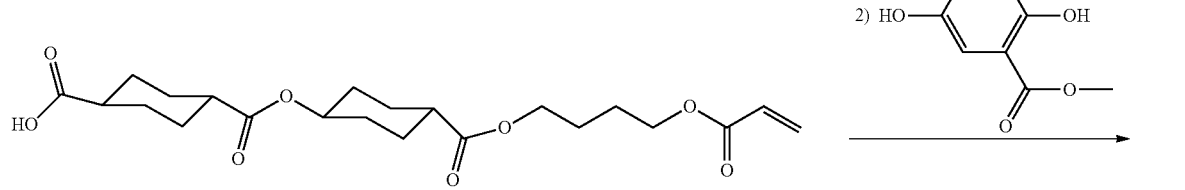

Carboxylic Acid Derivative 1

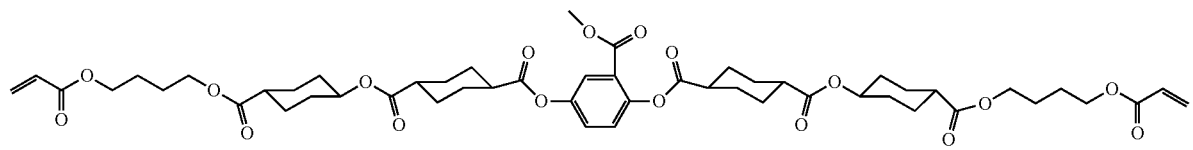

<Formation of Phase Difference Film>

[Preparation of Coating Sample]

A liquid crystalline composition coating liquid (1) having compositions described below was prepared by using the exemplary compounds synthesized in the examples described above.

| | |
|---|---|
| Compound (1-3) | 80 parts by mass |
| Compound (1-20) | 20 parts by mass |
| Air Interface Alignment Agent (A) | 0.1 parts by mass |
| Polymerization Initiator IRGACURE819 (manufactured by BASF SE) | 3 parts by mass |
| Solvent Chloroform | 900 parts by mass |

Air Interface Alignment Agent (A)

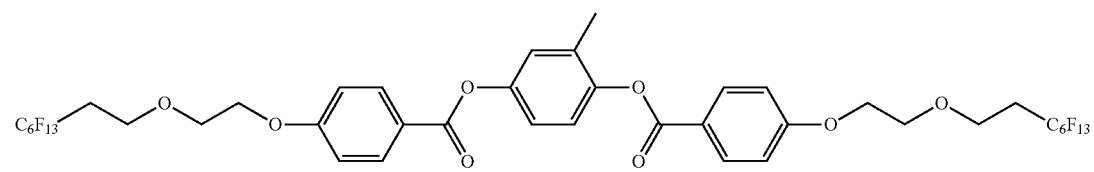

A polyimide alignment film SE-130 manufactured by Nissan Chemical Industries, Ltd. was applied onto a washed glass substrate by using a spin coating method, was dried, and then, was calcined at 250° C. for 1 hour. This was subjected to a rubbing treatment, and thus, a substrate with an alignment film was prepared. The polymerizable composition coating liquid described above was applied onto a rubbing treatment surface of the alignment film of the substrate at a room temperature by a spin coating method, was heated at 80° C. for 1 minute, and then, was left to stand at room temperature for 10 minutes, and thus, a coating sample of Example 1 was prepared.

Coating samples of Examples 2 and 5 to 7 and Comparative Example 1 were prepared by the same method as that in Example 1 except that the polymerizable compound of the polymerizable composition coating liquid (1) described above (the compound 1-3 and the compound 1-20) was changed as shown in the following table.

A coating sample of Example 3 was prepared by the same method as that in Example 1 except that a liquid crystalline composition coating liquid (3) having compositions described below was used instead of the liquid crystalline composition coating liquid (1) described above.

| Coating liquid (3) | |
|---|---|
| Liquid crystal composition (MI-1) | 100 parts by mass |
| Air Interface Alignment Agent (A) | 0.1 parts by mass |
| Polymerization Initiator IRGACURE819 (manufactured by BASF SE) | 3 parts by mass |
| Solvent Chloroform | 900 parts by mass |

A coating sample of Example 4 was prepared by the same method as that in Example 1 except that a liquid crystalline composition coating liquid (4) having compositions described below was used instead of the liquid crystalline composition coating liquid (1) described above.

| Coating liquid (4) | |
|---|---|
| Liquid crystal composition (MI-1) | 50 parts by mass |
| Compound (1-3) | 50 parts by mass |
| Air Interface Alignment Agent (A) | 0.1 parts by mass |

-continued

| Coating liquid (4) | |
|---|---|
| Polymerization Initiator IRGACURE819 (manufactured by BASF SE) | 3 parts by mass |
| Solvent Chloroform | 900 parts by mass |

[Haze Test]

The haze of the coating samples of Examples 1 to 7 and Comparative Example 1 after being left to stand was measured by a hazemeter (NDH2000, manufactured by NIPPON DENSHOKU INDUSTRIES CO., LTD.). The haze of the coating sample of Example 1 was 0.35. Evaluation results of each of the samples are shown in Table 2 such that the haze of greater than or equal to 1 is evaluated as C, the haze of greater than or equal to 0.6 and less than 1 is evaluated as B, the haze of greater than or equal to 0.4 and less than 0.6 is evaluated as A, and the haze of less than 0.4 is evaluated as S.

[Δn Measurement]

A polyimide alignment film SE-130 manufactured by Nissan Chemical Industries, Ltd. was applied onto a washed glass substrate by a spin coating method, was dried, and then, was calcined at 250° C. for 1 hour. This was subjected to a rubbing treatment, and thus, a substrate with an alignment film was prepared. The liquid crystalline composition coating liquid (1) was applied onto a rubbing treatment surface of the prepared substrate with an alignment film at a room temperature by a spin coating method, was aligned and matured at 80° C. for 1 minute, and then, was subjected to light irradiation at 50° C. for 30 seconds under an atmosphere of nitrogen gas by using a high pressure mercury lamp, and the alignment was immobilized, and thus, a phase difference film of Example 1 was formed. The precipitation of the crystals was not observed on a coated film during a period from the coating to the polymerization.

As a result of measuring the prepared phase difference film in a Tip-Tilt mode by using AxoScan manufactured by Axometrics, Inc, it was confirmed that the average tilt angle of the liquid crystal calculated by the device was 3.8 degrees, and thus, it was possible to form an A-plate type phase difference film. In addition, a phase difference (Re) measured by using the device was 64.5 nm.

In addition, a film thickness (d) measured by using a non-contact three-dimensional surface shape measurement system (BW-A501, manufactured by Nikon Corporation) was 1.52 m, and Δn (Re/d) at a wavelength of 550 nm calculated from a ratio of the phase difference (Re) to the film thickness (d) was 0.043.

Phase difference films of Examples 2 and 5 to 7 and Comparative Example 1 were prepared by the same method as that in Example 1 except that the polymerizable compound of the polymerizable composition coating liquid (1) described above (the compound 1-3 and the compound 1-20) was changed as shown in the following table. Phase difference films of Examples 3 and 4 were respectively prepared by the same method as that in Example 1 except that the liquid crystalline composition coating liquid (3) and the liquid crystalline composition coating liquid (4) having compositions described above were used instead of the liquid crystalline composition coating liquid (1) described above. For each of the prepared phase difference films of Examples 2 to 7 and Comparative Example 1, in the same manner as that in Example 1, a phase difference and a film thickness were measured and Δn was calculated. The results are shown in Table 2. Furthermore, in Comparative Example 1, the precipitation of the crystals was observed during a period from the coating to the polymerization.

TABLE 2

| | Group A | | Group B | | | Re | d | |
|---|---|---|---|---|---|---|---|---|
| | Compound No. | Parts by Mass | Compound No. | Parts by Mass | Haze Test | (nm) | (μm) | Δn |
| Example 1 | 1-3 | 80 | 1-20 | 20 | S | 0.35 | 64.5 | 1.52 | 0.043 |
| Example 2 | 1-3 | 90 | 1-20 | 10 | S | 0.26 | 66.8 | 1.56 | 0.043 |
| Example 3 | 1-3 | 78 | 1-34 | 22 | S | 0.32 | 82.8 | 1.54 | 0.053 |
| Example 4 | 1-3 | 89 | 1-34 | 11 | S | 0.34 | 75.9 | 1.62 | 0.044 |
| Example 5 | 1-3 | 80 | 56 | 20 | A | 0.48 | 72.3 | 1.59 | 0.045 |
| Example 6 | 1-3 | 80 | 70 | 20 | A | 0.52 | 65.6 | 1.57 | 0.042 |
| Example 7 | 1-20 | 20 | 56 | 80 | B | 0.70 | 65.1 | 1.63 | 0.040 |
| Comparative Example 1 | 1-3 | 100 | None | | C | 10.5 | 66.8 | 1.56 | 0.043 * |

* Precipitation Occurs

<Formation of Selective Reflection Film (101)>

A liquid crystalline composition coating liquid (101) having compositions described below was prepared by using the exemplary compounds synthesized as described above.

| | |
|---|---|
| Coating liquid (101) | |
| Liquid crystal composition (MI-1) | 100 parts by mass |
| Chiral Agent LC-756 (manufactured by BASF SE) | 5.5 parts by mass |
| Air Interface Alignment Agent (A) | 0.02 parts by mass |
| Air Interface Alignment Agent (B) | 0.02 parts by mass |
| Polymerization Initiator IRGACURE819 (manufactured by BASF SE) | 3 parts by mass |
| Solvent Methyl Acetate | 260 parts by mass |
| Cyclohexanone | 40 parts by mass |

Air Interface Alignment Agent (B)

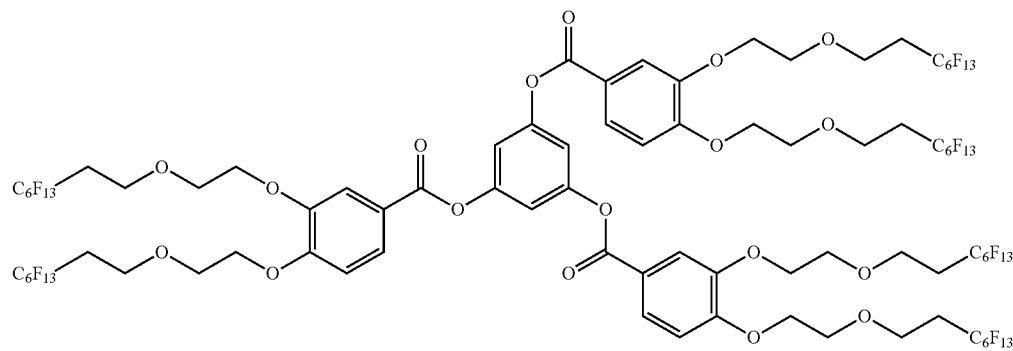

A polymerizable composition coating liquid (101) was applied onto a rubbing treatment surface of PET manufactured by Fujifilm Corporation, which had been subjected to a rubbing treatment, at a room temperature by using a wire bar such that the thickness of the dried film after being dried became 3.0 µm. The coated layer was dried at a room temperature for 30 seconds, then was heated at an atmosphere of 75° C. for 2 minutes, and was subjected to UV irradiation at 50° C. under an atmosphere of nitrogen gas by using a high pressure mercury lamp such that irradiation dose became 300 mJ/cm², and thus, a selective reflection film (101) was obtained. The precipitation of the crystals was not observed on a coated film during a period from the coating to the heating.

The selective reflection film (101) was observed by a polarizing microscope, and thus, uniform alignment without alignment defect was confirmed. A transmission spectrum of the film was measured by using a spectrophotometer UV-3100PC manufactured by SHIMADZU CORPORATION, and thus, the transmission spectrum had a selective reflection peak having a center at 462 nm, and a half-width of the selective reflection peak was 25 nm. A ratio ($\Delta\lambda/\lambda$) of the half-width of the selective reflection wavelength range to the center wavelength of the selective reflection was 0.054.

<Formation of Laminated Selective Reflection Film>

Liquid crystalline composition coating liquids (102), (103), and (104) having compositions described below were respectively prepared by using the exemplary compounds synthesized as described above.

| Coating liquid (102) | |
|---|---|
| Liquid crystal composition (MI-1) | 100 parts by mass |
| Chiral Agent LC-756 (manufactured by BASF SE) | 3.7 parts by mass |
| Air Interface Alignment Agent (A) | 0.02 parts by mass |
| Air Interface Alignment Agent (B) | 0.02 parts by mass |
| Polymerization Initiator IRGACURE819 (manufactured by BASF SE) | 3 parts by mass |
| Solvent Methyl Acetate | 260 parts by mass |
| Cyclohexanone | 40 parts by mass |

| Coating liquid (103) | |
|---|---|
| Liquid crystal composition (MI-1) | 100 parts by mass |
| Chiral Agent LC-756 (manufactured by BASF SE) | 4.6 parts by mass |
| Air Interface Alignment Agent (A) | 0.01 parts by mass |
| Air Interface Alignment Agent (B) | 0.005 parts by mass |
| Polymerization Initiator IRGACURE819 (manufactured by BASF SE) | 3 parts by mass |
| Solvent Methyl Acetate | 260 parts by mass |
| Cyclohexanone | 40 parts by mass |

| Coating liquid (104) | |
|---|---|
| Liquid crystal composition (MI-1) | 100 parts by mass |
| Chiral Agent LC-756 (manufactured by BASF SE) | 5.5 parts by mass |
| Air Interface Alignment Agent (A) | 0.01 parts by mass |
| Air Interface Alignment Agent (B) | 0.005 parts by mass |
| Polymerization Initiator IRGACURE819 (manufactured by BASF SE) | 3 parts by mass |
| Solvent Methyl Acetate | 260 parts by mass |
| Cyclohexanone | 40 parts by mass |

The polymerizable composition coating liquid (102) was applied onto a rubbing treatment surface of PET manufactured by Fujifilm Corporation, which had been subjected to a rubbing treatment, at a room temperature by using a wire bar such that the thickness of the dried film after being dried became 4.8 µm. The coated layer was dried at a room temperature for 30 seconds, and then, was heated at an atmosphere of 75° C. for 2 minutes, and was subjected to UV irradiation at 60° C. under an atmosphere of nitrogen gas by using a high pressure mercury lamp such that irradiation dose became 300 mJ/cm², and thus, a selective reflection film (102) was obtained.

Subsequently, the polymerizable composition coating liquid (103) was applied onto the surface of a liquid crystal layer of the selective reflection film (102) at a room temperature by using a wire bar such that the thickness of the dried film after being dried became 4.0 µm (the total film thickness including the thickness of the underlayer was 8.8 µm). The coated layer was dried at a room temperature for 30 seconds, and then, was heated at an atmosphere of 75° C. for 1 minute, and was subjected to UV irradiation at 60° C. by using a high pressure mercury lamp under an atmosphere of nitrogen gas such that irradiation dose became 300 mJ/cm², and thus, a selective reflection film (103) was obtained.

Further, the polymerizable composition coating liquid (104) was applied onto the surface of a liquid crystal layer of the selective reflection film (103) at a room temperature by using a wire bar such that the thickness of the dried film after being dried became 3.0 µm (the total film thickness including the thickness of the underlayer was 11.8 µm). The coated layer was dried at a room temperature for 30 seconds, and then, was heated at an atmosphere of 75° C. for 1 minute, and was subjected to UV irradiation at 60° C. by using a high pressure mercury lamp under an atmosphere of nitrogen gas such that irradiation dose became 300 mJ/cm², and thus, a selective reflection film (104) was obtained.

A transmission spectrum of the selective reflection film (104) was measured by using a spectrophotometer UV-3100PC manufactured by SHIMADZU CORPORATION, and thus, it was found that the transmission spectrum had a selective reflection peak at each of 651 nm, 532 nm, and 464 nm, and had high visible light transmittance of greater than or equal to 80%.

What is claimed is:

1. A polymerizable composition, comprising:
   at least two types of polymerizable compounds represented by Formula (I):

$$Q^1-Sp^1-\{A-L\}_{m-1}A-Sp^2-Q^2 \quad (I)$$

in the formula, A represents a phenylene group which may have a substituent or a trans-1,4-cyclohexylene group which may have a substituent,
   L represents a single bond or a linking group selected from the group consisting of —CH$_2$O—, —OCH$_2$—, —(CH$_2$)$_2$OC(=O)—, —C(=O)O(CH$_2$)$_2$—, —C(=O)O—, —OC(=O)—, —OC(=O)O—, —CH=CH—C(=O)O—, and —OC(=O)—CH=CH—,
   m represents an integer of 3 to 12,
   Sp$^1$ and Sp$^2$ each independently represent a single bond or a linking group selected from the group consisting of a linear alkylene group or a branched alkylene group having 1 to 20 carbon atoms, and a group in which one or two or more —CH$_2$—'s in the linear alkylene group or the branched alkylene group having 1 to 20 carbon atoms are substituted with —O—, —S—, —NH—, —N(CH$_3$)—, —C(=O)—, —OC(=O)—, or —C(=O)O—, and Q$^1$ and Q$^2$ each independently represent a hydrogen atom or a polymerizable group selected from the group consisting of groups represented by Formula Q-1 to Formula Q-5, and any one of Q$^1$ and Q$^2$ represents a polymerizable group,

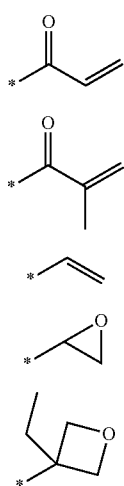

wherein in a case where a number obtained by dividing the number of trans-1,4-cyclohexylene groups which may have a substituent and are represented by A by m is set to mc, mc's for the two types of polymerizable compounds are different from each other, at least one of the two types of the polymerizable compounds satisfies 0.5<mc<0.65, and at least the other of the two types of the polymerizable compounds satisfies 0.5<mc, and the polymerizable composition comprises at least one compound of Formula (I) in which:
(i) m represents an integer of 6 to 12, and
(ii) in a case where a number obtained by dividing the number of trans-1,4-cyclohexylene groups which may have a substituent and are represented by A by m is set to mc, 0.5<mc<0.7 is satisfied.

2. The polymerizable composition according to claim 1, wherein in Formula (I), the substituent that the phenylene group and the trans-1,4-cyclohexylene group may have is selected from the group consisting of an alkyl group, an alkoxy group, and a group represented by —C(=O)—X$^3$—Sp$^3$-Q$^3$, and here, X$^3$ represents a single bond, —O—, —S—, or —N(Sp$^4$-Q$^4$)—, or represents a nitrogen atom which forms a ring structure along with Q$^3$ and Sp$^3$, Sp$^3$ and Sp$^4$ each independently represent a single bond or a linking group selected from the group consisting of a linear alkylene group or a branched alkylene group having 1 to 20 carbon atoms, and a group in which one or two or more —CH$_2$—'s in the linear alkylene group or the branched alkylene group having 1 to 20 carbon atoms are substituted with —O—, —S—, —NH—, —N(CH$_3$)—, —C(=O)—, —OC(=O)—, or —C(=O)O—, and Q$^3$ and Q$^4$ each independently represent a hydrogen atom, a cycloalkyl group, a group in which one or two or more —CH$_2$—'s in the cycloalkyl group are substituted with —O—, —S—, —NH—, N(CH$_3$)—, —C(=O)—, —OC (=O)—, or —C(=O)O—, or any one polymerizable group selected from the group consisting of groups represented by Formula Q-1 to Formula Q-5.

3. The polymerizable composition according to claim 1, wherein the polymerizable composition includes at least one type of the compound which is represented by Formula (I) and has a partial structure represented by Formula (II);

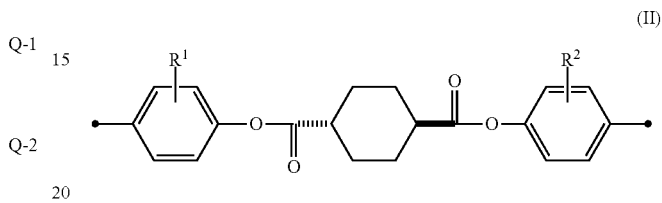

in the formula, R$^1$ and R$^2$ are each independently selected from the group consisting of a hydrogen atom, an alkyl group, an alkoxy group, and a group represented by —C(=O)—X$^3$—Sp$^3$-Q$^3$, and here, X$^3$ represents a single bond, —O—, —S—, or —N(Sp$^4$-Q$^4$)—, or represents a nitrogen atom which forms a ring structure along with Q$^3$ and Sp$^3$, Sp$^3$ and Sp$^4$ each independently represent a single bond or a linking group selected from the group consisting of a linear alkylene group or a branched alkylene group having 1 to 20 carbon atoms, and a group in which one or two or more —CH$_2$—'s in the linear alkylene group or the branched alkylene group having 1 to 20 carbon atoms are substituted with —O—, —S—, —NH—, —N(CH$_3$)—, —C(=O)—, —OC(=O)—, or —C(=O)O—, and Q$^3$ and Q$^4$ each independently represent a hydrogen atom, a cycloalkyl group, a group in which one or two or more —CH$_2$—'s in the cycloalkyl group are substituted with —O—, —S—, —NH—, —N(CH$_3$)—, —C(=O)—, —OC (=O)—, or —C(=O)O—, or any one polymerizable group selected from the group consisting of groups represented by Formula Q-1 to Formula Q-5.

4. The polymerizable composition according to claim 3, wherein R$^1$ and R$^2$ are each independently —C(=O)—X$^3$-Sp$^3$-Q$^3$, and X$^3$ is —O—.

5. The polymerizable composition according to claim 3, wherein R$^1$ and R$^2$ are identical to each other.

6. The polymerizable composition according to claim 1, wherein all of the polymerizable compounds satisfy 0.5<mc<0.65.

7. The polymerizable composition according to claim 1, wherein the compounds represented by Formula (I) are compounds represented by Formula (V):

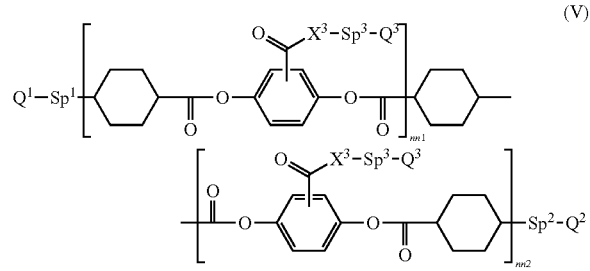

in the formula, nn1 and nn2 each independently represent an integer of 1 or 2 and values represented by nn1+nn2 in the two types of the polymerizable compounds are different from each other.

8. The polymerizable composition according to claim 1, further comprising:
one or more selected from a group consisting of a cross-linking agent and a polymerization initiator.

9. The polymerizable composition according to claim 1, further comprising:
a chiral compound.

10. A film, comprising:
a layer obtained by curing the polymerizable composition according to claim 1.

11. A film, comprising:
two or more layers obtained by curing the polymerizable composition according to claim 1.

12. The film according to claim 10,
wherein the film exhibits selective reflection, and Δλ/λ which is a ratio of a half-width Δλ of a wavelength range of the selective reflection to a center wavelength λ of the selective reflection is less than or equal to 0.09.

13. The film according to claim 10,
wherein the film reflects visible light.

14. A film, comprising:
at least three layers obtained by curing the polymerizable composition according to claim 1,
wherein the three layers are a layer formed by immobilizing a cholesteric liquid crystalline phase having a center wavelength of selective reflection in a red light wavelength range, a layer formed by immobilizing a cholesteric liquid crystalline phase having a center wavelength of selective reflection in a green light wavelength range, and a layer formed by immobilizing a cholesteric liquid crystalline phase having a center wavelength of selective reflection in a blue light wavelength range.

15. A half mirror for displaying a projection image, comprising:
the film according to claim 14.

16. The half mirror for displaying a projection image according to claim 15, further comprising:
a base material which is inorganic glass or an acrylic resin.

17. The half mirror for displaying a projection image according to claim 15, further comprising:
an antireflection layer on an outermost surface.

18. A polymerizable compound which is represented by Formula (I):

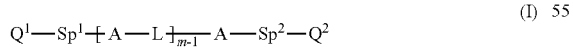

in the formula, A represents a phenylene group which may have a substituent or a trans-1,4-cyclohexylene group which may have a substituent,
L represents a single bond or a linking group selected from the group consisting of —CH$_2$O—, —OCH$_2$—, —(CH$_2$)$_2$OC(=O)—, —C(=O)O(CH$_2$)$_2$—, —C(=O)O—, —OC(=O)—, —OC(=O)O—, —CH=CH—C(=O)O—, and —OC(=O)—CH=CH—, m represents an integer of 6 to 12,
in a case where a number obtained by dividing the number of trans-1,4-cyclohexylene groups which may have a substituent and are represented by A by m is set to mc, 0.5<mc<0.7 is satisfied,
Sp$^1$ and Sp$^2$ each independently represent a single bond or a linking group selected from the group consisting of a linear alkylene group or a branched alkylene group having 1 to 20 carbon atoms, and a group in which one or two or more —CH$_2$—'s in the linear alkylene group or the branched alkylene group having 1 to 20 carbon atoms are substituted with —O—, —S—, —NH—, —N(CH$_3$)—, —C(=O)—, —OC(=O)—, or —C(=O)O—, and
Q$^1$ and Q$^2$ each independently represent a hydrogen atom or a polymerizable group selected from the group consisting of groups represented by Formula Q-1 to Formula Q-5, and any one of Q$^1$ and Q$^2$ represents a polymerizable group:

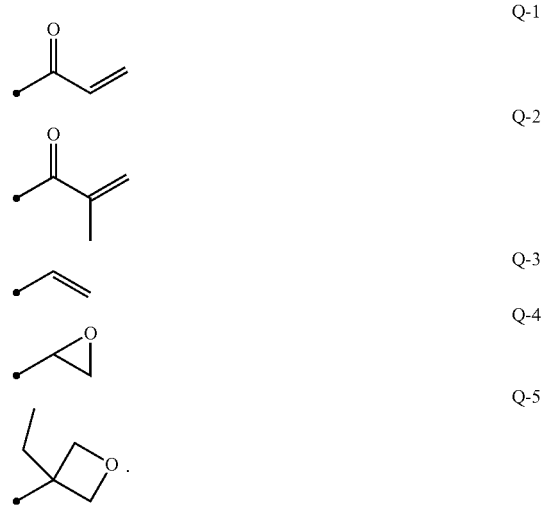

19. The polymerizable compound according to claim 18, wherein m is 7 or 9.

20. The polymerizable compound according to claim 19, which is represented by Formula (V):

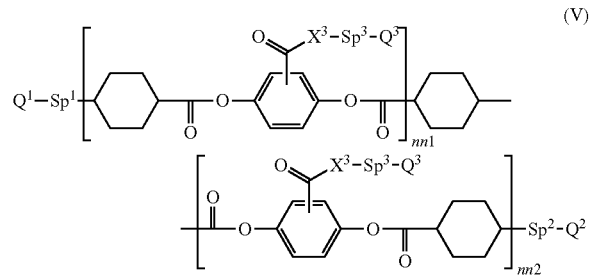

in the formula, Sp$^1$ and Sp$^2$ each independently represent a single bond or a linking group selected from the group consisting of a linear alkylene group or a branched alkylene group having 1 to 20 carbon atoms, and a group in which one or two or more —CH$_2$—'s in the linear alkylene group or the branched alkylene group having 1 to 20 carbon atoms are substituted with —O—, —S—, —NH—, —N(CH₃)—, —C(=O)—, —OC(=O)—, or —C(=O)O—, Q¹ and Q² each independently represent a hydrogen atom or a polymerizable group selected from the group consisting of groups represented by Formula Q-1 to Formula Q-5, and any one of Q¹ and Q² represents a polymerizable group,

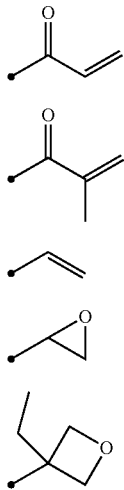

Q-1

Q-2

Q-3

Q-4

Q-5

X³ represents a single bond, —O—, —S—, or —N(Sp⁴-Q⁴)—, or represents a nitrogen atom which forms a ring structure along with Q³ and Sp³, Sp³ and Sp⁴ each independently represent a single bond or a linking group selected from the group consisting of a linear alkylene group or a branched alkylene group having 1 to 20 carbon atoms, and a group in which one or two or more —CH₂—'s in the linear alkylene group or the branched alkylene group having 1 to 20 carbon atoms are substituted with —O—, —S—, —NH—, —N(CH₃)—, —C(=O)—, —OC(=O)—, or —C(=O)O—, and Q³ and Q⁴ each independently represent a hydrogen atom, a cycloalkyl group, a group in which one or two or more —CH₂—'s in the cycloalkyl group are substituted with —O—, —S—, —NH—, —N(CH₃)—, —C(=O)—, —OC(=O)—, or —C(=O)O—, or any one polymerizable group selected from the group consisting of groups represented by Formula Q-1 to Formula Q-5, and nn1 and nn2 each independently represent an integer of 1 or 2, and nn1+nn2 is 3 or 4.

* * * * *